United States Patent
Schwintner et al.

(10) Patent No.: US 11,389,488 B2
(45) Date of Patent: Jul. 19, 2022

(54) STOOL COLLECTION METHOD AND SAMPLE PREPARATION METHOD FOR TRANSPLANTING FECAL MICROBIOTA

(71) Applicant: MAAT PHARMA, Lyons (FR)

(72) Inventors: Carole Schwintner, Lyons (FR); Alice Leroux, Lyons (FR); Clémence Mader, Lyons (FR); Hervé Affagard, Lyons (FR)

(73) Assignee: MAAT PHARMA, Lyons (FR)

( * ) Notice: Subject to any disclaimer, the term of this patent is extended or adjusted under 35 U.S.C. 154(b) by 0 days.

(21) Appl. No.: 16/979,077

(22) PCT Filed: Mar. 8, 2019

(86) PCT No.: PCT/FR2019/050522
§ 371 (c)(1),
(2) Date: Sep. 8, 2020

(87) PCT Pub. No.: WO2019/171012
PCT Pub. Date: Sep. 12, 2019

(65) Prior Publication Data
US 2020/0405776 A1    Dec. 31, 2020

(30) Foreign Application Priority Data
Mar. 9, 2018 (FR) ...................... 1852084

(51) Int. Cl.
*A61K 35/74* (2015.01)
*A61K 35/00* (2006.01)

(52) U.S. Cl.
CPC ........ *A61K 35/74* (2013.01); *A61K 2035/115* (2013.01)

(58) Field of Classification Search
None
See application file for complete search history.

(56) References Cited

FOREIGN PATENT DOCUMENTS

WO    2016170285 A1    10/2016
WO    2018026913 A1    2/2018

OTHER PUBLICATIONS

Machine translation of Affagard et al (WO2016/170285), pp. 1-9, 2016.*
International Search Report received in PCT/FR2019/050522, dated Jun. 12, 2019, pp. 1-7.
Paramsothy et al., "Mulidonor Intensive Faecal Microbiota Transplantation for Active Ulcerative Colitis: A Randomised Placebo-Controlled Trial", Lancet, (2017), vol. 389, No. 10075, pp. 1218-1228.
Jacob et al., "Single Delivery of High-Diversity Fecal Microbiota Preperation by Colonoscopy is Safe and Effective in Increasing Microbial Diversity in Active Ulcerative Colitis", Inflammatory Bowel Diseases, (2017), vol. 23, No. 6, pp. 1-18.
Kazuhiko Kakihana et al., "Fecal microbiota transplantation for patients with steroid-resistant acute graft-versus-host disease of the gut," Blood, vol. 128, No. 16, Oct. 20, 2016, pp. 2083-2088.

* cited by examiner

*Primary Examiner* — Brian Gangle
(74) *Attorney, Agent, or Firm* — ArentFox Schiff LLP

(57) ABSTRACT

The present invention relates to a method for preparing a homogeneous mixture of fecal microbiota from at least two preselected donors. The homogeneous mixture of fecal microbiota thus obtained has a bacterial diversity and an increased viability. The homogeneous mixture of fecal microbiota may be used for treating intestinal dysbiosis and for treating pathologies associated with such dysbiosis.

15 Claims, 10 Drawing Sheets

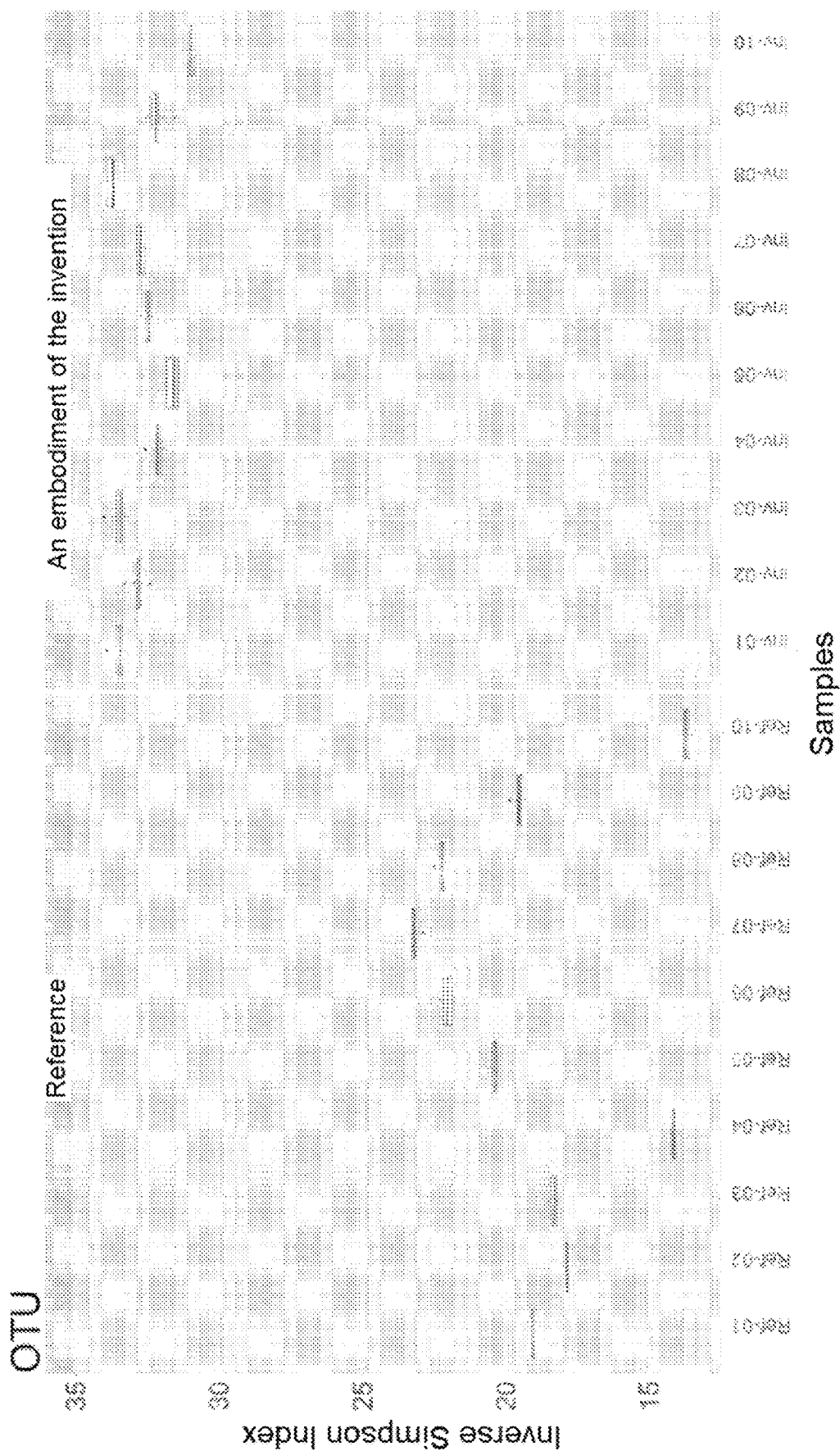

STOOL COLLECTION METHOD AND SAMPLE PREPARATION METHOD FOR TRANSPLANTING FECAL MICROBIOTA

CROSS-REFERENCE TO RELATED APPLICATIONS

This application is a National Stage Entry of PCT/FR2019/050522, filed Mar. 8, 2019, which claims foreign priority to FR Patent Application No. 1852084, filed on Mar. 9, 2018, the disclosure of which is hereby incorporated by reference in its entirety.

The present invention relates to a procedure for collecting stools from several donors and method for the preparation of a sample of fecal microbiota.

The invention also relates to use of said sample in the transplantation of fecal microbiota (FMT, also called fecal microbiota transplant), preferably for treating intestinal dysbioses.

Human intestinal microbiota, commonly called "intestinal flora", is the set of microorganisms (bacteria, yeasts and fungi) which are found in the human gastrointestinal system (stomach, intestine and colon). The bacterial diversity is currently estimated at approximately $10^3$ bacterial species constituting the dominant intestinal microbiota of an adult individual, with an abundance of $10^{14}$ bacteria, representing a bacterial metagenome of 200,000 to 800,000 genes in each individual, i.e. 10 to 50 times the number of genes in the human genome. Sterile in utero, the intestine is colonized from the first days of life, until developing towards a unique individual microbiota. Each person has bacteria that are relatively close in terms of species, but the exact composition of their microbiota (species, proportions) is in large part (over ⅔ of the species) specific to the host. Thus, the human intestinal microbiota is a very diversified and complex ecosystem, specific to each individual.

Maintaining broad diversity of the microbiota promotes the stability thereof. However, certain pathologies or treatments destabilize the microbiota: antibiotics for example, as well as diseases with an inflammatory component, such as chronic inflammatory bowel diseases (CIBD), can limit the diversity of the microbiota in the intestine. Antibiotic treatments (or antibiotherapy), in particular, result in alteration of the microbiota, which may favor the proliferation of pathogenic organisms such as *Clostridium difficile*.

A certain number of pathologies are associated with intestinal dysbiosis, for example graft-versus-host disease (GvHD). Allogenic graft or allogenic transplantation of hematopoietic stem cells (allo-HSCT) is an effective treatment for hematopoietic malignancies and hereditary hematopoietic disorders, and is considered to be the most effective cancer immunotherapy to date [Sung, A. D. and Chao, N. J. (2013), Concise Review: Acute Graft-Versus-Host Disease: Immunobiology, Prevention, and Treatment, Stem Cells Transl. Med. 2: 25-32]. However, the T-lymphocytes derived from transplanted stem cells can attack the recipient host tissues, leading to GvHD, a major complication of allo-HSCT associated with significant mortality (15 to 25% of deaths after allo-HSCT). Patients undergoing allo-HSCT may simultaneously be exposed to cytotoxic chemotherapy, whole body irradiation, immunosuppressants and broad-spectrum antibiotics, which may cause significant alterations of the intestinal microbiota. In fact, a significant enrichment in Enterococcaceae, as well as an increase in Lactobacillales and a reduction in Clostridiales, is often observed in patients after allo-HSCT. As a consequence, commonly encountered dominant bacteria, such as vancomycin-resistant *Enterococcus, viridans* group streptococci and various Proteobacteria, can enter the bloodstream and cause septicemia. It is noteworthy that this change is particularly significant in patients who subsequently develop a refractory graft-versus-host disease (GvHD) [Holler et al. (2014), Biol Blood Marrow Transplant. 20(5): 640-645, and Peled, J. (2017) 59$^{th}$ Annual Meeting of the American Society of Hematology, Atlanta, USA, December 9-11].

In order to reestablish the intestinal microbiota and thus reestablish homeostasis (i.e. symbiosis), fecal microbiota transplantation (FMT) is envisaged and tested. It consists of the introduction of stools from a healthy donor into the digestive tract of a recipient patient, in order to restabilize the altered intestinal microbiota of the host. This fecal microbiota transplant may be allogenic (i.e. from a healthy donor individual to a patient) or autologous (i.e. from an individual to her- or himself). The results obtained on infections of the *Clostridium difficile* type are encouraging, and some patients have been successfully treated (Tauxe et al., Lab Medicine, Winter 2015, volume 46, Issue 1). Recent studies have also shown that GvHD patients treated with FMT have had an improvement in gastro-intestinal symptoms and a reduction or cessation of diarrhea, associated with reconstruction of the microbiota Kakihana et al. (2017) Transplantation 128: 2083-2089, and Spindelboeck et al. (2017) Hematologica 102: e210.

In the case of allogenic transplantation, it is important for the transplanted sample to have an acceptable profile in terms of viability and diversity of the bacteria, as the suspension of microbiota in its diluent represents the active ingredient (active substance) of the medicament. Current transplantation methods are often empirical and take no particular precautions to ensure the diversity of the bacteria present in the samples of fecal microbiota used, or for best preserving the viability of the anaerobic bacteria that are the majority constituents of the intestinal microbiota.

American patent application US 2017/239303 describes compositions for restoration of the intestinal microbiota, as well as methods for the manufacture and administration thereof. This document discloses that the compositions comprising samples have a Shannon diversity index of approximately 0.4-2.5 where the calculations are carried out at the "family" level. Depending on the taxonomic level (phyla, species, etc.) at which the calculation is carried out it is approximately 1-8.

The publication by Paramsothy et al. [Paramsothy S., et al. (2017), Multidonor intensive faecal microbiota transplantation for active ulcerative colitis: a randomised placebo-controlled trial, Lancet, March 25; 389(10075): 1218-1228] describes the preparation of fecal microbiota compositions in the treatment of active ulcerative colitis. The compositions are produced by mixing and homogenization of the stools from 3-7 donors, then an aqueous saline solution is added to the mixture obtained (see page 122 left-hand column, "Methods"). FIG. 3 in the publication by Paramsothy et al. (top right-hand panel) shows the phylogenetic diversity of the compositions. A large variance still exists between the batches produced (indicated by "Donor batches" in the Figure), even after having pooled the donor stool samples. This variance seems as large as that between the individual donors (indicated by "Individual Donors" in the Figure). Thus, a considerable heterogeneity exists between the samples intended for treating patients. Such heterogeneity is undesirable for a pharmaceutical composition. Indeed, in order to ensure that the patient responds in the same way to each dose (or sample) of fecal microbiota received, it is necessary for the doses to be as homogenous as possible, and that the batches are also homogenous.

There is thus a need to provide a method for the transplantation of fecal microbiota that is safe, reproducible, efficacious and easy to implement, in particular at industrial scale. Moreover, there is a need to provide a method for the transplantation of fecal microbiota in which the bacterial diversity of the transplanted products is as high as possible and in which there is homogeneity between the different doses (samples) of products transplanted to the same person. Thus, it is necessary for there to be homogeneity between the different doses originating from the same batch of fecal microbiota (intra-batch homogeneity) and between the different batches produced (inter-batch homogeneity). The viability of the bacteria must be preserved as far as possible throughout the method and during storage.

It is necessary to provide samples of fecal microbiota having optimal bacterial diversity and viability for administration in the treatment and prevention of bacterial intestinal dysbiosis (iatrogenic or non-iatrogenic) and/or associated pathologies. There is a need to provide a method for the preparation of such samples. The pathologies concerned can be refractory graft-versus-host disease (GvHD), *Clostridium difficile* infection, ulcerative colitis, inflammatory bowel disease, irritable bowel syndrome, Crohn's disease, type II diabetes, food allergies, cancer, including leukemia, obesity and morbid obesity. Other pathologies associated with dysbiosis include autism, sclerosis, traveler's diarrhea, chronic vaginal infection (cystitis, mycoses), bone and joint infections, dysbiosis associated with intensive care in hospital, Parkinson's disease, Alzheimer's disease, schizophrenia, intestinal dysbiosis associated with antineoplastic chemotherapy or immunotherapy, dysbiosis linked to alcohol or non-alcohol-related liver diseases.

There is a need to provide samples of fecal microbiota for use in the treatment or the prevention of iatrogenic intestinal dysbiosis and/or the associated pathologies and complications comprising, but not limited to, septicemia, septic shock and gastrointestinal disorders, including but not limited to diarrhea, mucitis, abdominal pain and gastrointestinal bleeding.

The present invention responds to the above-described needs.

Therefore, a purpose of the invention is to provide samples of fecal microbiota having optimal diversity and sufficient bacterial viability for use thereof in FMT (fecal microbiota transplantation), and which can easily be produced reliably and reproducibly.

The invention relates to a method for the preparation of a homogenous mixture of fecal microbiota originating from at least two preselected donors comprising the following steps:
 a. taking at least one sample of fecal microbiota from said preselected donors,
 b. within a time period of less than 5 minutes after taking the sample, placing the sample obtained in a) in an oxygen-impermeable collection device,
 c. quality control of the samples taken, and exclusion of samples that do not meet the quality criteria,
 d. to each of the samples retained after the quality control step c), adding an aqueous saline solution comprising at least one cryoprotectant and/or a bulking agent,
 e. filtering the samples obtained at the end of step d) to form a series of inocula,
 f. pooling said inocula to form a mixture of inocula,
 g. homogenization of said mixture obtained in step f), in particular by manual stirring or using a stirring device, steps b) and d) to g) being carried out under anaerobiosis.

According to an embodiment of the invention, the donors are preselected according to the following preselection criteria:
 i. age between 18 and 60 years,
 ii. body mass index (BMI) between 18 and 30,
 iii. absence of personal medical history of serious infectious diseases, such as AIDS, hepatitis, etc., metabolic and neurological disorders, or depression,
 iv. absence of recently taking medicaments capable of degrading the composition of the intestinal microbiota,
 v. absence of recent occurrence of symptoms associated with a gastrointestinal disease such as fever, diarrhea, nausea, vomiting, abdominal pain, jaundice; absence of any history of serious infectious diseases, in particular AIDS, hepatitis, etc.
 vi. absence of recent travel in tropical countries,
 vii. absence of at-risk sexual behavior,
 viii. absence of recent wound, piercing and/or tattoo (typically, in the last three months),
 ix. absence of recent chronic fatigue (typically, in the last three months),
 x. absence of recent allergic reaction (typically, in the last three months),
 xi. optionally, having a varied diet.

According to an embodiment of the invention, the quality criteria of the samples in step c) comprise:
 consistency of the sample between 1 and 6 on the Bristol scale,
 absence of blood or urine in the sample.

According to an embodiment of the invention, the quality criteria of the samples in step c) comprise:
 absence of the following bacteria: *Campylobacter, Clostridium difficile* (A/B toxin), *Salmonella, Yersinia enterocolitica, Vibrio* sp., Shiga toxin-producing *E. coli* (STEC) stx1/stx2, multi-resistant bacteria, bacteria producing extended-spectrum beta-lactamases (ESBL)-glycopeptide/vancomycin resistant Enterococci (GRE/VRE), *Listeria monocytogenes*, and carbapenem-resistant bacteria,
 absence of the following parasites: *Cryptosporidium parvum, Cyclospora* sp., *Entamoeba histolytica, Giardia lamblia, Blastocystis hominis, Helminths, Strongyloides stercoralis, Isospora* sp., *Microsporidia* and *Dientamoeba fragilis*,
 absence of the following viruses: adenovirus F40/41, astrovirus, norovirus, rotavirus A, sapovirus and picornavirus (aichi virus and enterovirus),
 absence of the following bacteria: enteroaggregative *E. coli* (EAEC), enteropathogenic *E. coli* (EPEC), enterotoxigenic *E. coli* (ETEC) lt/st, *Shigella*/enteroinvasive *E. coli* (EIEC) and *Plesiomonas shigelloides*.

According to an embodiment of the invention, the at least one cryoprotectant and/or bulking agent in step d) is a polyol, a di-, tri- or polysaccharide or mixture thereof and a bulking agent.

According to an embodiment of the invention, the aqueous saline solution in step d) comprises maltodextrin and trehalose.

According to an embodiment of the invention, the filtration in step e) is carried out with a filter comprising pores of diameter less than or equal to 0.5 mm, preferably less than or equal to 265 µm.

According to an embodiment of the invention, the time between collection of the sample and the end of step g) is less than 76 hours.

According to an embodiment of the invention, step g) of homogenization is carried out at a temperature between 2° C. and 25° C., preferably between approximately 2 and 6° C., more preferentially at approximately 4° C.

According to an embodiment of the invention, the method comprises the following transfer step:

h. transferring the homogenized mixture obtained in step g):
  i. to pouches for storage at a temperature of approximately −50° C. to −80° C., preferably, at −80° C., or for storage at a temperature between approximately 2 to 6° C. for use of the mixture within approximately 16 hours, or for storage at a temperature between 10 to 25° C. for use of the mixture within approximately 4 hours,
  ii. to a lyophilization device for lyophilization.

According to an embodiment of the invention, the homogenous mixture of fecal microbiota originates from at least four donors, preferably at least five donors.

According to another aspect, the invention relates to use of the homogenous mixture of fecal microbiota capable of being obtained according to the method of the invention in the transplantation of allogenic fecal microbiota (FMT).

According to an embodiment of the invention, the homogenous mixture of fecal microbiota originates from at least four donors and contains the following butyrate-producing bacterial genera: *Blautia, Faecalibacterium, Alistipes, Eubacterium, Bifidobacterium, Ruminococcus, Clostridium, Coprococcus, Odoribacter, Roseburia, Holdemanella, Anaerostipes, Oscillibacter, Subdoligranulum* and *Butyrivibrio*.

According to an embodiment of the invention, said homogenous mixture of fecal microbiota has a high diversity, having an Inverse Simpson index greater than 15, preferably greater than 20.

The invention relates to use of the homogenous mixture of fecal microbiota capable of being obtained according to the method of the invention in the treatment of intestinal dysbioses.

The invention relates to use of the homogenous mixture of fecal microbiota capable of being obtained according to the method of the invention in the treatment of graft-versus-host disease (GvHD).

The invention relates to use of the homogenous mixture of fecal microbiota capable of being obtained according to the method of the invention in the treatment of iatrogenic intestinal dysbiosis and/or associated pathologies and complications comprising septicemia, septic shock and gastrointestinal disorders, including intestinal inflammation, diarrhea, mucitis, abdominal pain and gastrointestinal bleeding.

The invention relates to use of the homogenous mixture of fecal microbiota capable of being obtained according to the method of the invention in the treatment of *Clostridium difficile* infection and associated diarrhea (CDI), inflammatory bowel disease (IBD), irritable bowel syndrome (IBS), idiopathic constipation, coeliac disease, Crohn's disease, obesity and morbid obesity, autism, multiple sclerosis, traveler's diarrhea, chronic vaginal infection (including cystitis and mycosis), bone and joint infections, Parkinson's disease, type II diabetes, food allergies, cancer, resistant leukemia, Alzheimer's disease, schizophrenia and bipolar disorders, intestinal dysbiosis associated with antineoplastic chemotherapy or immunotherapy and alcohol- or non-alcohol-related liver disease.

DESCRIPTION OF THE FIGURES

FIG. 4a: The richness (number of bacterial species) measured for the individual inocula and also for the mixture of inocula for batches, batch No. 1 to batch No. 4. The operational taxonomic units (OTU's) were assessed with 16S ribosomal RNA (16S rRNA). For individual donors, the richness is between 100 and 350 species.

FIG. 4b: The Bray-Curtis similarity of the individual inocula per batch ("Donors") the inocula compared between batches ("Inter-batch") and the pooled inocula in the pouches in the same batch ("Intra-batch").

FIG. 6 represents the diversity measured according to the Inverse Simpson index in the two groups of samples in Example 3 in the form of box-plots. FIG. 6a shows the diversity of each sample and FIG. 6b shows the diversity of the two groups of samples.

DETAILED DESCRIPTION

Figure 1:
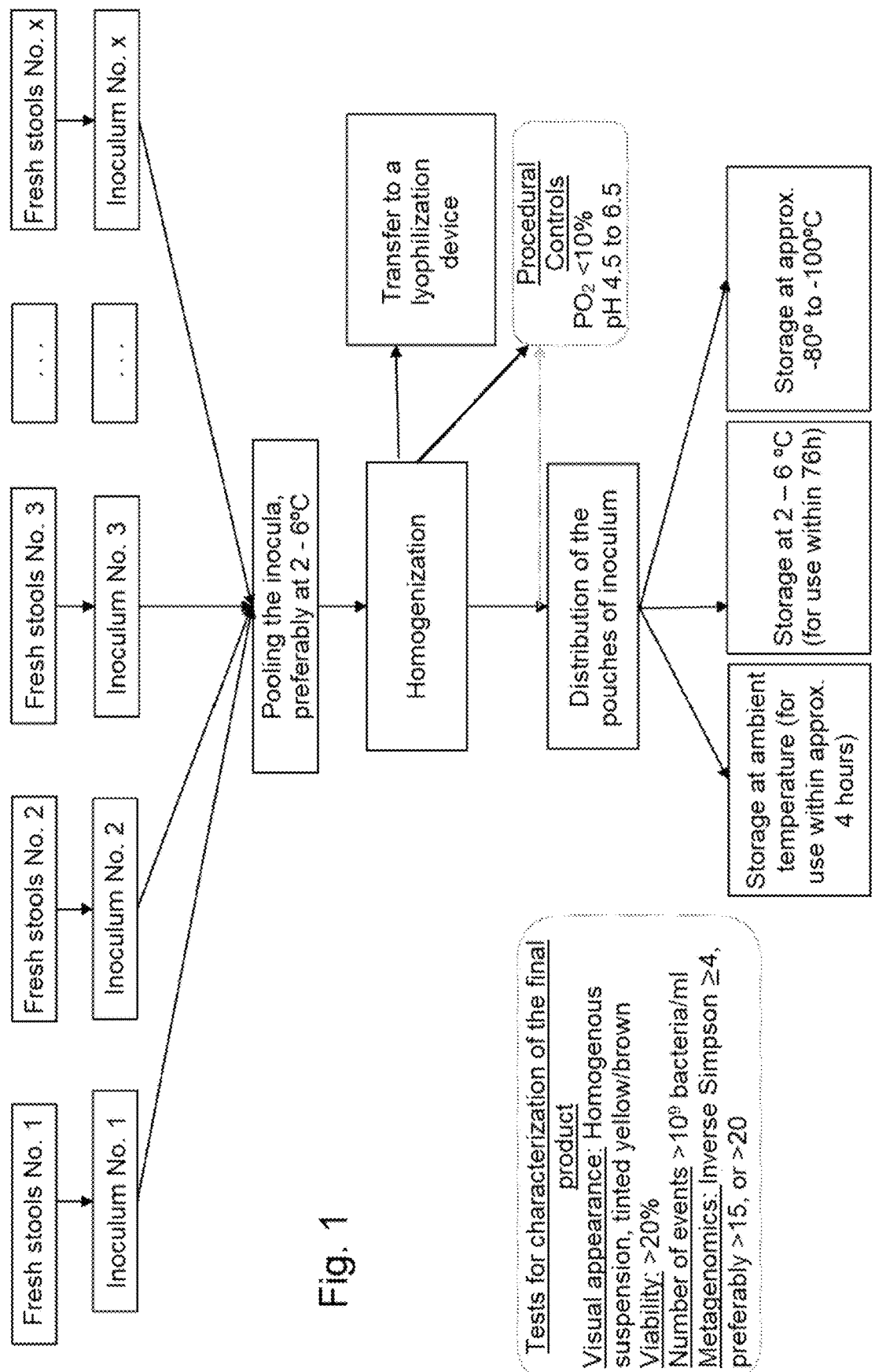
FIG. 1 is a diagrammatic representation of the method for the preparation of a homogenous mixture of fecal microbiota from samples of fecal microbiota from several donors for use in allogenic FMT.

The present invention relates to a method for the collection and preparation of a homogenous mixture of fecal microbiota from several donors. The invention also relates to use of said homogenous mixture in the transplantation of allogenic fecal microbiota, in particular for treating intestinal dysbioses, and in particular the diseases associated with such dysbioses.

In general, according to the invention, the donors are healthy human subjects. By "healthy subject" is meant a subject not suffering from an imbalance of the intestinal microbiota or a pathology diagnosed/recognized by the medical profession.

Thus, for selecting potential donors, a certain number of criteria have been defined. These criteria are as follows:
  i. age between 18 and 60 years,
  ii. body mass index (BMI) between 18 and 30,
  iii. absence of personal medical history of serious infectious diseases, such as AIDS or viral hepatitis, metabolic and neurological disorders, or depression,
  iv. absence of recently (during approximately the 3 months preceding the donation) taking medicaments capable of degrading the composition of the intestinal microbiota, such as antibiotics,
  v. absence of recent (during approximately the 3 months preceding the donation) occurrence of symptoms associated with a gastrointestinal disease such as fever, diarrhea, nausea, vomiting, abdominal pain, jaundice; absence of any history of serious infectious diseases, in particular AIDS, hepatitis, etc.
  vi. absence of recent (during approximately the 3 months preceding the donation) travel in tropical countries,
  vii. absence of at-risk sexual behavior,
  viii. absence of recent (during approximately the 3 months preceding the donation) contact with human blood, for example via a wound, piercing and/or tattoo,
  ix. absence of recent (during approximately the 3 months preceding the donation) chronic fatigue,
  x. absence of recent (during approximately the 3 months preceding the donation) allergic reaction,
  xi. optionally, having a varied diet.

The criteria for selection of the donors are based on those in general use in Europe for blood donation, but with additional criteria specific to stool donation and to the context of the transplantation of fecal microbiota. Thus, criteria (i) to (xi) were defined for selecting donors.

The purpose of the optional criterion relating to the varied diet is to enhance the ability to have a wide bacterial diversity in the sample of fecal microbiota. It is therefore preferable for the donor to have a varied diet.

By "varied diet" is meant a diet consisting of varied vegetables and different cereals (which will allow regular intake of fibers), but also fruits and meats.

By "bacterial diversity" is meant the diversity or variability measured at the level of the genus or species. Bacterial diversity can be expressed with terms such as "richness" (number of species observed in a sample), "Shannon index" and "Simpson index". The Shannon index gives an idea of the specific diversity, i.e. the number of species in the sample (specific richness) and of the distribution of the individuals within these species (specific equitability). The Simpson index is derived from the richness and takes account of the relative abundance of each species. It is comprised between 0 (low diversity) and 1 (high diversity). The Inverse Simpson index makes it possible to reflect the diversity (by considering the richness and relative abundance of the species as for the Simpson index) with a range of values ranging from 0 (low diversity) to infinity (high diversity).

The method according to the invention typically comprises a step a) of taking at least one stool sample, comprising the fecal microbiota, from the donor subject. Step a) of taking at least one stool sample can thus be carried out by the donor her- or himself, for example at home, or by a health professional.

Taking at least one stool sample is preferably carried out with a collection device designed for this function, in such a way that the stool sample is enclosed in an anaerobic environment. Thus, the collection device described in patent application WO2016/170290 may be mentioned. Thus, typically, a device for the collection of stools at home is delivered to the selected donors with a user guide. Preferably, a stool sample has a weight of at least 20 g.

Following this step of taking the sample, and within a rapid timescale, for example less than 5 minutes after taking the sample, preferably less than 3 minutes, more preferentially less than 1 minute, the sample is placed in an oxygen-impermeable collection device: this is step b).

According to an embodiment of the invention, the step of taking at least one sample of fecal microbiota is carried out by depositing a stool sample directly into a collection device, such as that described in patent application WO2016/170290.

Then, the method is generally carried out under anaerobiosis (under anaerobic atmosphere) from this point, or under containment where exposure to air is limited. The control step c) can be carried out under anaerobiosis or under aerobiosis or under containment where exposure to air is limited. According to an embodiment of the invention, taking the sample in order to undertake quality control testing is carried out under aerobiosis. According to an embodiment of the invention, steps b) and d) to g) of the method are carried out under anaerobiosis or under containment where exposure to air is limited. By limiting the exposure to air, the viability of the bacteria constituting the fecal microbiota and present in the sample is thus preserved.

Preferably, the airtight collection device is presented in the form of the type comprising:
  a container comprising a body which contains an inner space suitable for receiving the sample of fecal microbiota from the donor subject, and a neck which delimits an access opening to the inner space of the body, and
  a lid suitable for being mounted in a tight and removable manner on the neck of the container, in such a way as to close the access opening of the neck and to close the inner space of the body, in which the body of the container is constituted by a flexible pouch, and in which at least one from the container and the lid is provided with an evacuation facility suitable for evacuating at least a part of the gases contained within the inner space of the body of the container.

Preferably, the evacuation facility of the device comprises a passage made through either the container or the lid, and a component for closing the passage in order to prevent external fluids from entering the inner space of the body of the container. Preferably, the evacuation facility of the device also comprises a microporous filtration membrane arranged in the passage.

Alternatively, the airtight collection device is presented in the form of the type comprising:
  a container comprising a body which contains an inner space suitable for receiving the sample of fecal microbiota from the donor subject, and a neck which delimits an access opening to the inner space of the body, and
  a lid suitable for being mounted in a tight and removable manner on the neck of the container, in such a way as to close the access opening of the neck and to close the inner space of the body, in which the inner space of the body of the container optionally contains a chemical device neutralizing oxygen.

For example, in order to carry out steps a) to d) (or e)) of the method, according to an embodiment of the invention, it is possible to use a collection device equipped with at least one additional device for example, an additional filler device suitable for filling the inner space with fluid (for example, the solution added in step d)), as described in document WO 2016/170290.

Furthermore, the additional device can also be an analysis tube, used for withdrawing a sample for analysis (for example quality control according to step c)).

Preferably, the airtight collection device is used for steps a) and b): taking the sample in step a) is carried out directly from said device, in particular from the container, and closing the device, in particular by means of the lid, places the sample under an oxygen-free atmosphere (step b)).

In particular, the device mentioned above, used in step b), makes it possible to carry out steps b), d) and e) under anaerobiosis.

Optionally, a transportation step may thus take place. This transportation step makes it possible to return the sample from the location where it was taken to the laboratory, for subsequent processing and analysis.

After step b), preferably, within 24 hours after step b), quality control step c) is carried out on the samples taken. The purpose of this quality control is to eliminate samples of fecal microbiota which do not meet the predefined quality criteria. Thus, the samples retained after the quality control are considered to be acceptable for forming the desired homogenous mixture of fecal microbiota.

In general, the controlled quality criteria comprise:
consistency of the sample between 1 and 6 on the Bristol scale, by visual inspection,
absence of blood or urine in the sample.

The criteria can also include:
absence of the following bacteria: *Campylobacter, Clostridium difficile* (A/B toxin), *Salmonella, Yersinia enterocolitica, Vibrio* sp., Shiga toxin-producing *E. coli* (STEC) stx1/stx2, multi-resistant bacteria: bacteria producing extended-spectrum beta-lactamases (ESBL)-glycopeptide/vancomycin resistant Enterococci (GRE/VRE), *Listeria monocytogenes* and carbapenem-resistant Bacteria,
absence of the following parasites: *Cryptosporidium parvum, Cyclospora* sp., *Entamoeba histolytica, Giardia lamblia, Blastocystis hominis, Helminths, Strongyloides stercoralis, Isospora* sp., *Microsporidia* and *Dientamoeba fragilis*,
absence of the following viruses: adenovirus F40/41, astrovirus, norovirus, rotavirus A, sapovirus and picornavirus (aichi virus and enterovirus),
absence of the following bacteria: enteroaggregative *E. coli* (EAEC), enteropathogenic *E. coli* (EPEC), enterotoxigenic *E. coli* (ETEC) lt/st, *Shigella* enteroinvasive *E. coli* (EIEC) and *Plesiomonas shigelloides*.

Control of the consistency of the sample is carried out in general by visual inspection. If the sample has an appearance between 1 and 6, preferably 5, on the Bristol scale, [Lewis, S. J.; Heaton, K. W. (September 1997). "Stool form scale as a useful guide to intestinal transit time". Scand. J. Gastroenterol.], it is acceptable and will be retained.

Control of the absence of blood or urine in the sample can be carried out by visual inspection or by other means. For example, rapid immunological tests can be used. For example, the OC Sensor® test (available from MAST Diagnostic in France), a quantitative immunological test which detects hemoglobin by means of human globin-specific antibodies.

If the presence of blood and/or urine is found, the sample is eliminated.

According to an embodiment of the invention, control of the sample for the absence of certain parasites, viruses and bacteria can also be carried out. Typically, control of the sample for the absence of certain parasites, viruses and bacteria is carried out once per week, per donor. This means that typically, for a donor who supplies, for example, five samples during the week, one sample out of five will be controlled. According to an embodiment of the invention, the step of control of the sample for the absence of certain parasites, viruses and bacteria is carried out on each sample.

Controls for the absence of certain bacteria, certain parasites and certain viruses from the samples are carried out according to the methods known to a person skilled in the art.

Preferably, the following bacteria must be absent from the sample: *Campylobacter, Clostridium difficile* (A/B toxin), *Salmonella, Yersinia enterocolitica, Vibrio* sp., Shiga toxin-producing *E. coli* (STEC) stx1/stx2, *Listeria monocytogenes* and multi-resistant bacteria, such as gram-negative bacteria producing extended-spectrum beta-lactamases (ESBL) and glycopeptide/vancomycin resistant Enterococci (GRE/VRE), *Listeria monocytogenes*, carbapenem-resistant Bacteria, enteroaggregative *E. coli* (EAEC), enteropathogenic *E. coli* (EPEC), enterotoxigenic *E. coli* (ETEC) lt/st, *Shigella*/enteroinvasive *E. coli* (EIEC) and *Plesiomonas shigelloides*.

Preferably, the aforementioned bacteria are pathogens the presence of which in the collected sample of fecal microbiota will exclude the donor of said sample from the selection.

Similarly, the following parasites should preferably be absent from the sample of fecal microbiota: *Cryptosporidium, Cyclospora cayetanensis, Entamoeba histolytica* and *Giardia lamblia, Blastocystis hominis, Helminths, Strongyloides stercoralis, Isospora* sp., *Microsporida* and *Dientamoeba fragilis*.

Similarly, the following viruses should preferably be absent from the sample of fecal microbiota: adenovirus F40/41, astrovirus, norovirus, rotavirus A, sapovirus and picornavirus (aichi virus and enterovirus).

Controls for the presence of bacteria, parasites and viruses are carried out according to the methods known to a person skilled in the art. By way of example, the following methods may be mentioned: culture under selective conditions, detection of the bacteria, parasites or viruses with antibodies, amplification (with PCR for example) and analysis of the DNA sequences present in samples. There may be mentioned as an analysis system for the DNA sequences the FilmArray® system from BioMerieux (France), an automated system that can be used for the detection of bacteria, parasites and viruses. For example, the following parasites can be detected by means of this system: *Cryptosporidium, Cyclospora cayetanensis, Entamoeba histolytica* and *Giardia lamblia*. The "Allplex-GI" PCR test series available from Eurobio (France) may also be mentioned.

Other parasites such as *Blastocystis hominis, Isospora* sp., *Microsporidia* and *Dientamoeba fragilis* can be detected by microscopic examination with concentration of the sample if necessary. *Strongyloides stercoralis* can be detected with, for example, elective staining, after sample concentration if necessary.

Multi-resistant bacteria, such as ESBL, VRE and GRE, can be detected by cultures under specific conditions, for example the commercially available ESBL, VRE or ALOA media, for example from BioMerieux.

For certain species of bacteria and viruses, the absence thereof from the sample is not required. According to an embodiment of the invention, the presence of the following bacteria is not a criterion for exclusion of the sample: enteroaggregative *E. coli* (EAEC), enteropathogenic *E. coli* (EPEC), enterotoxigenic *E. coli* (ETEC) lt/st, *Shigella*/ enteroinvasive *E. coli* (EIEC) and *Plesiomonas shigelloides*. According to an embodiment of the invention, the presence of the EBV virus is not a criterion for exclusion as this virus is prevalent today in the general human population.

Generally, the samples retained after the control step c), which comprises a control for the absence of blood or urine in the sample, and optionally, a control for the absence of certain parasites, viruses and bacteria from the sample, pass to step d). Step d) comprises the addition of a cryoprotective diluent.

Generally, for step d), the samples are transformed separately into liquid inocula by adding cryoprotective diluent. Generally, an aqueous saline solution comprising at least one cryoprotectant and/or a bulking agent is added to each of the samples retained after the quality control step c).

Any suitable diluent/cryoprotectant may be used for the preparation of the inocula. Preferably, polyols or di-, tri- or polysaccharides, or a mixture thereof, may be used. There may be mentioned as polyol, glycerol, mannitol, sorbitol, propylene glycol or ethylene glycol. As di-, tri- or polysaccharides, there may be mentioned dimers, trimers, tetramers and pentamers of different or identical units, said units being selected from glucose, fructose, galactose, fucose and N-acetylneuraminic acid. Among the disaccharides capable of use there may be mentioned trehalose, or one of the analogues thereof, or saccharose. Preferably, the cryoprotectant is selected from glycerol, mannitol, sorbitol, propylene glycol, ethylene glycol, trehalose and analogues thereof, saccharose, galactose-lactose and mixtures thereof. More preferably, the cryoprotectant is galactose-lactose or trehalose.

Typically, the quantity of cryoprotectant present in the aqueous saline solution is comprised between 3 and 30% by weight with respect to the total volume of the final inoculum (wt/vol), preferably between 4 and 20% (wt/vol).

There may be mentioned as bulking agents, for example the partial hydrolysates of starch, in particular of wheat or maize, as well as the partial hydrolysates of starchy foods, for example of potato, containing large quantities of maltodextrin. Preferably, the bulking agent is a mixture of maltodextrins, in which maltodextrin is present between 3 and 30%, preferably between 4 and 20% (with respect to the total volume of the final inoculum (weight/volume).

According to an embodiment of the invention, le diluent/ cryoprotectant is an aqueous saline solution comprising at least one cryoprotectant and a bulking agent.

Typically, the solution contains water and physiologically acceptable salts. Typically, the solution will contain calcium, sodium, potassium or magnesium salts with ferrous chlorides, gluconates, acetates or hydrogencarbonates. The aqueous saline solution can optionally also contain at least one antioxidant. The antioxidant can be selected from ascorbic acid and salts thereof, tocopherols, cysteine and salts thereof, in particular hydrochloride, and mixtures thereof. Preferentially, the aqueous saline solution comprises at least one salt selected from sodium chloride, calcium chloride, magnesium chloride, potassium fluoride, sodium gluconate and sodium acetate, and optionally at least one antioxidant selected from sodium L-ascorbate, tocopherol, cysteine hydrochloride monohydrate and mixtures thereof. Typically, the salt is present in the aqueous saline solution at a concentration comprised between approximately 5 and 20 g/l, preferably between 7 and 10 g/l (with respect to the total volume of the final inoculum). Typically, the antioxidant is present in the aqueous saline solution in a quantity comprised between 0.3 and 1% by weight/volume, preferably between 0.4 and 0.6% by weight/volume (with respect to the total volume of the final inoculum).

Generally, the aqueous saline solution comprising at least one cryoprotectant and/or a bulking agent is added to the sample of fecal microbiota with the ratio weight (g)/volume (ml) comprised between 1:0.5 and 1:10, preferably between 1:2 and 1:8, more preferentially 1:4. By a sample: solution weight/volume ratio equal to 0.5 weight:10 volumes is meant that the sample is mixed at 0.5 weight (for example 0.5 g) for 10 volumes of solution (for example 10 ml).

Preferably, step d) of addition of an aqueous saline solution comprising at least one cryoprotectant and/or a bulking agent is carried out under anaerobiosis or under containment where exposure to air is limited. According to an embodiment of the invention, the saline solution comprising at least one cryoprotectant and/or a bulking agent is added in the additional device of the collection device mentioned below and the solution is added to the stool sample via a closed pipe. The mixture of the sample with at least an aqueous saline solution comprising at least one cryoprotectant and/or a bulking agent can in particular be carried out by mixing, in order to obtain a homogenous mixture.

The samples obtained after this dilution step are then filtered in step e). Preferably, the filtration step is carried out with one (or several, having increasingly small sized pores) filter(s) comprising pores of diameter less than or equal to 0.5 mm, preferably less than or equal to 265 µm. In the case where several filters are used, the size of the pores reduces progressively. Preferably, the first filters used comprise pores of diameter less than or equal to 2 mm, preferably less than or equal to 1 µm. Preferably, the last filter used comprises pores of a diameter less than or equal to 0.5 mm, preferably less than or equal to 265 µm. Thus, the individual inocula are obtained. Preferably, this filtration step e) is carried out under anaerobiosis, or under containment where exposure to air is limited. During filtration, the sample originating from step d) can be pressed through the filters manually, by mechanical action, by gravity, by vacuum or by other suitable means.

According to an embodiment of the invention, the same quantity (in terms of weight) of stools per donor is used to form the inoculum, i.e. for carrying out steps d) and e). There may be mentioned as suitable quantity for example, 25-80 g, preferably 40 g. Thus, each individual inoculum is produced by using the same sample quantity of fecal microbiota.

Step f) consists of pooling the inocula originating from filtration step e). In particular, typically, the individual inocula are transferred to a container, preferably, a flexible pouch. Typically, the volume of this container which pools inocula is from 1 L to 5 L, preferably of 3 L or 5 L. This volume can be greater according to the scale of industrialization of the method. The transfer can be carried out manually or by using mechanical means. Preferably, the transfer of the inocula is carried out by using mechanical means, for example, a syringe, more preferentially, with a peristaltic pump. Suitable peristaltic pumps are commercially available, for example from Interscience (France).

After pooling, the inocula are mixed so as to form a homogenous mixture (homogenization step g)). This homogenous mixture is thus considered to be a "batch" of fecal microbiota. Mixing the inocula can be carried out by any means. Mixing the inocula can be carried out manually or by mechanical means known to a person skilled in the art. There may be mentioned for example a platform shaker, available for example from Stuart (England).

In general, a rate of stirring of 80-200 rpm, preferably between 90 and 150 rpm, more preferentially 100-135 rpm, can be used. In general, homogenization can take place during a period of time comprised between 10 minutes and 2 hours, preferably 20 minutes and 1 hour, more preferentially for 30 minutes. The duration depends on the speed of stirring. A person skilled in the art knows how to determine the necessary homogenization time as a function of the homogenization method chosen. A colorimetric test can be used to verify if the mixture is homogenous. A visual inspection can also be used. Preferably, a colorimetric test followed by a visual inspection are carried out to determine if the mixture is homogenous.

The homogenization step can be carried out at a temperature between 2 and 25° C., preferably between 2° C. and 8° C., more preferentially at approximately 4° C.

According to an embodiment of the invention, an analysis step can be carried out on the homogenous mixture obtained after step g), before the mixture is stored or lyophilized (see details below). The pH and the $PO_2$ can be measured. The methods known to a person skilled in the art are used to carry out these measurements. Typically, the $PO_2$ of the mixture is less than 10%, preferably less than 5%, typically the pH is between 4 and 7, preferably between 4.5 and 6.5.

Preferably, less than 76 hours elapse between the start of step a) and the end of step g).

In general, the final product (the homogenous mixture) meets the following specifications:

Appearance: homogenous yellow/brown tinted suspension.

Viability: greater than 20%, preferably greater than 40% for lyophilization.

Number of (bacterial) events: greater than $10^9$ bacteria/ml.

Bacterial diversity: Inverse Simpson index greater than or equal to 4. Preferably, the Inverse Simpson index of the mixture of inocula is greater than or equal to 10, more preferentially, greater than 15, even more preferentially, greater than 20.

In general, the homogenous mixture is transferred (transfer step h) for storage or lyophilization. Thus, the mixture can be transferred to pouches:

for storage at a temperature of approximately −50° C. to −80° C., preferably, at approximately −80° C., for use of the mixture beyond 16 hours, or for storage at a temperature between 2 to 6° C. for use within approximately 16 hours, or for storage at a temperature between 10 to 25° C. for use of the mixture within the next four hours. Beyond four hours at ambient temperature, the number of bacteria increases and the homogeneity of the inoculum may be reduced.

Alternatively, the homogenous mixture can be transferred to a lyophilization device for subsequent or immediate lyophilization.

According to an embodiment of the invention, an analysis step i) can be carried out on the homogenous mixture obtained after the transfer step h) of the homogenous mixture to the storage location thereof (typically a pouch) or to the lyophilization location thereof (typically in a lyophilization device). Specifically, this analysis step comprises a visual inspection, viability measurements, a taxonomic analysis and measurements of numbers of events/ml. The aim of this analysis step is to determine if the sample meets the quality criteria for use thereof in FMT therapy.

Typically, the mixture has a yellow/brown color. Typically, the viability should be >20%. According to an embodiment of the invention, the viability is preferably >40%. If the mixture must be lyophilized, it is preferable for the viability to be >40%. In general, the cell concentration measured by flow cytometry is greater than $10^6$, preferably, greater than $10^7$ bacteria/ml, and more preferably greater than $10^9$ bacteria/ml. In terms of taxonomic analysis, in general it is preferable for the Shannon index to be greater than 3.5, preferably greater than 4.

The good quality of the mixture originating from the method according to an embodiment of the invention has been demonstrated by the applicants. The results of a qualitative evaluation of the method, according to an embodiment of the invention, carried out with six fresh stools from healthy donors, are shown in Example 1. Microbiota viability tests were carried out on each inoculum before pooling step f) and after homogenization step g).

The applicants have noted that the homogenous mixture constituted by the pooled inocula had its own bacterial viability, which is higher than would be expected.

Figure 2:
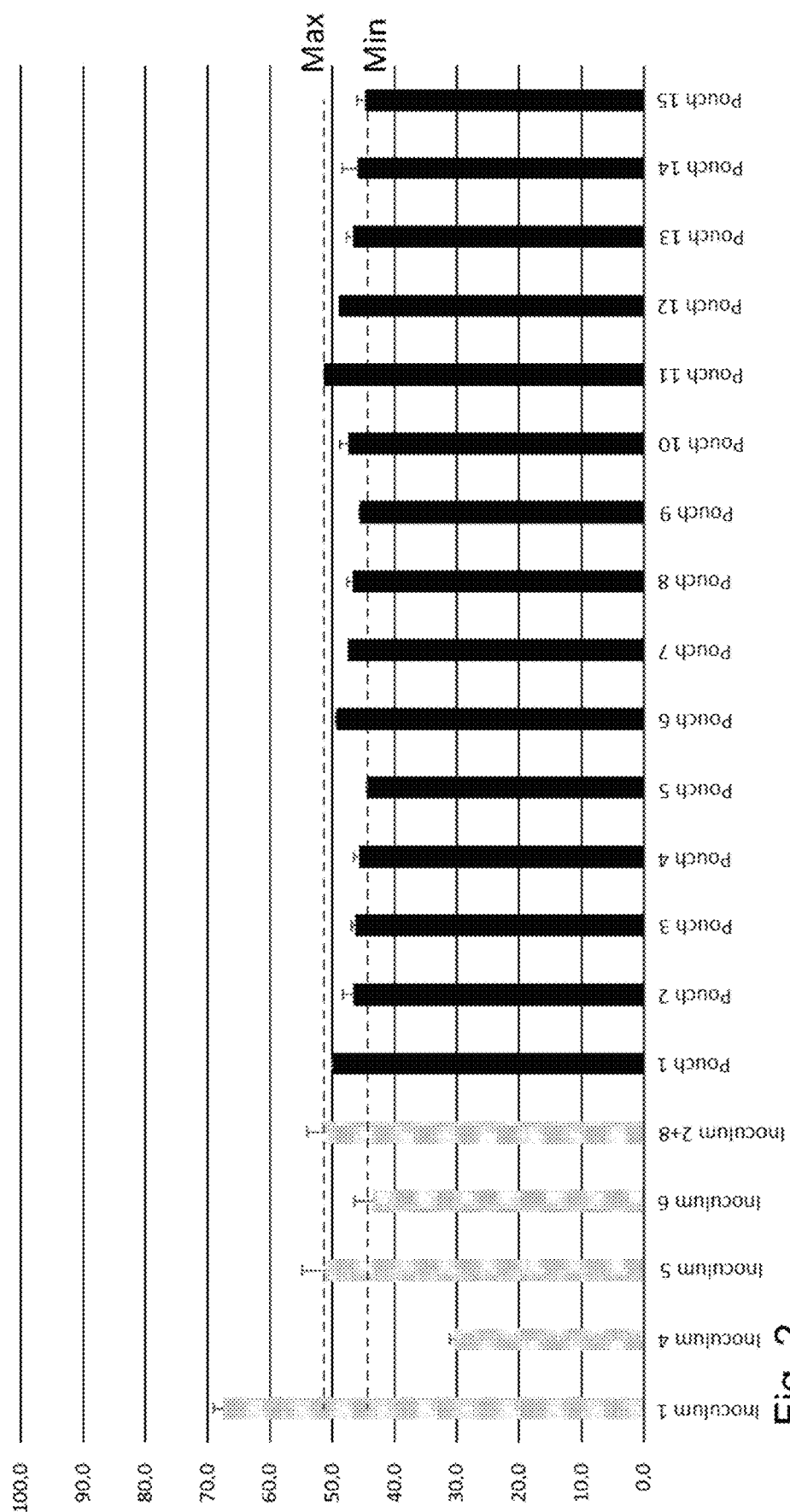
FIG. 2 is a histogram representing the percentage viability of the microbiota of the inoculum (inoculum 1, 4, 5, 6 and 2+8) and of the mixture of inoculum (active substance) in pouches 1 to 15 of inoculum for storage.

FIG. 2 is a histogram representing the percentage viability of the microbiota of the inocula of Example 1 (inoculum 1, 4, 5, 6 and 2+8) and of the mixture of inoculum (homogenous mixture) in pouches 1 to 15 of inoculum intended for storage. FIG. 2 shows that the individual inocula (inoculum 1, 4, 5, 6, 2+8) do not have the same individual viability, but that the mixture of inoculum has its own viability, different from the individual inocula. In addition, the method according to the invention ensures good reproducibility of the pouches of final mixture, since the viability of the microbiota is approximately the same for each pouch (greater than 40%).

Statistical analysis on the pouches of homogenous mixture indicates that there is no significant difference according to a t-test and according to a rank test, whether for the viability of the microbiota or for the number of events/μL. Thus, the applicants have shown that all the prepared pouches of mixture are mutually homogenous.

The results of a qualitative evaluation of the method, according to an embodiment of the invention, carried out with four different batches (Batch No. 1 to Batch No. 4) of fresh stools from healthy donors, are shown in Example 2. Batch No. 4 is the same batch as that used for Example 1 (and shown in FIG. 2). In Example 2, the number of donors is 2, 7, 4 and 6 for batch No. 1, batch No. 2, batch No. 3 and batch No. 4, respectively. The applicants measured the bacterial viability and diversity of the individual inocula (after step e)), of the homogenized pooled inocula (after step g)) and of the filled pouches before storage.

Figure 3:
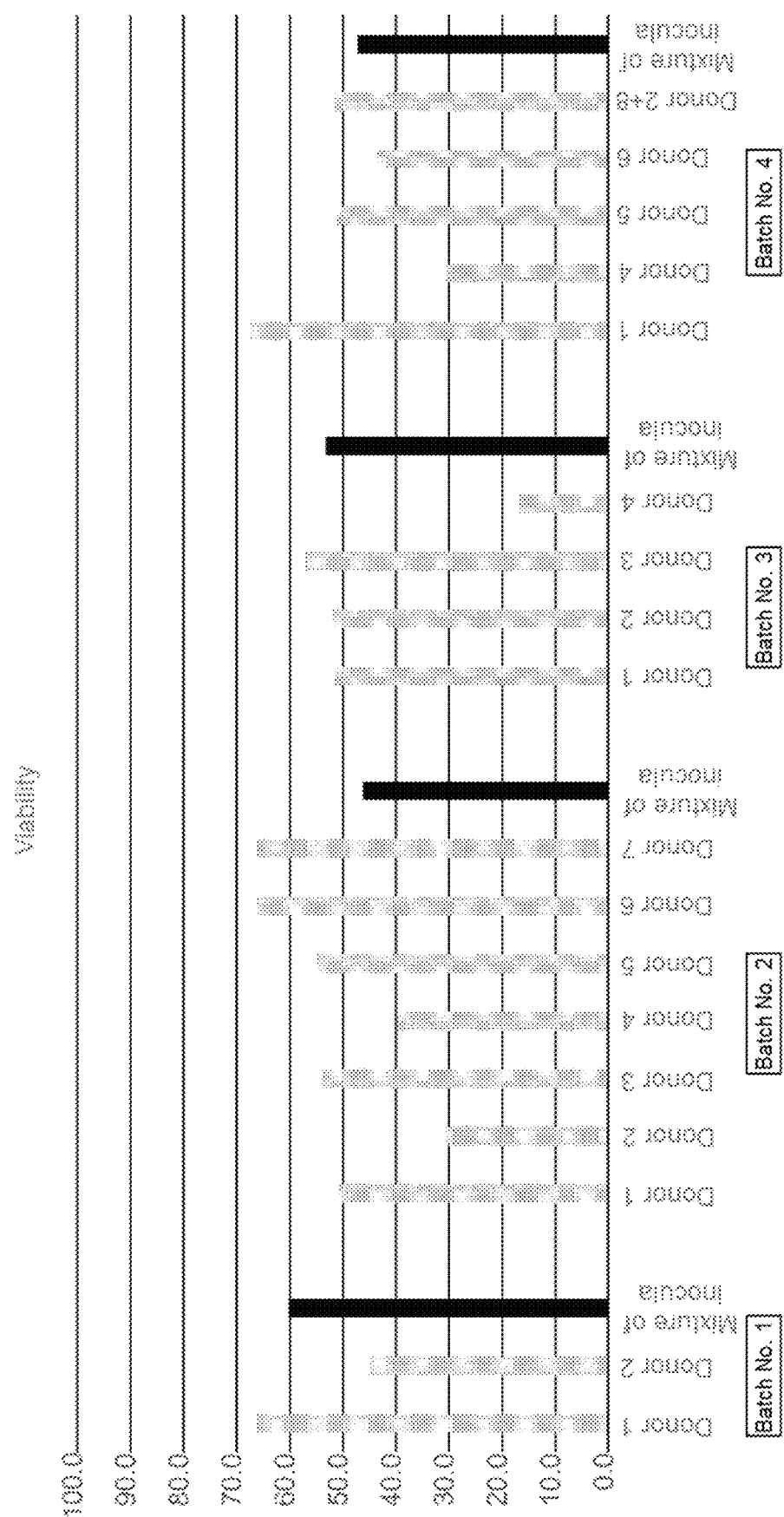
FIG. 3 is a histogram representing the percentage viability of the microbiota of the individual inocula and of the mixtures of inocula (pooled inocula) for four batches of product. Batch No. 4 is the same batch as that used for Example 1 (and shown in FIG. 2).

FIG. 3 again shows that the individual inocula vary, but that the mixture of inoculum has its own viability, different from the individual inoculum. The viability of the batches Nos. 1 to 4 is situated between 46.1% and 60.1%, which is excellent.

Figure 4A:
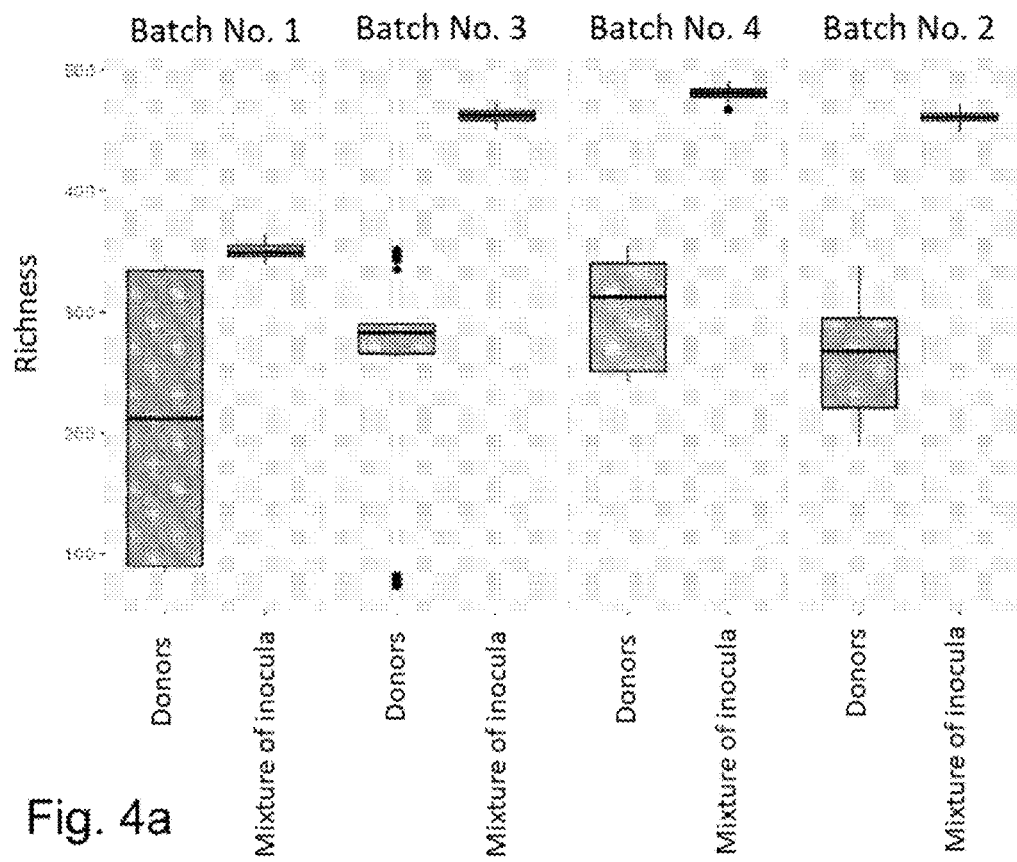
FIGS. 4a and 4b show the richness and the bacterial diversity of the inocula.

FIG. 4a shows the richness of the samples. The coefficient of variation (CV) was calculated for each inoculum. The CV (coefficient of variation or relative deviation) is a measurement of dispersion of the data around the mean. This is the calculation of the ratio of the standard deviation to the mean. The CV makes it possible to calculate the degree of variation of one sample from another. The smaller the CV value, the more homogenous or stable are the values. The CV of the individual inocula of the four batches varies between 16% and 81%. This difference is normal because it is known that individual microbiota are very different. For each pooled inoculum (originating from step g)), the coefficient of variation, per batch, is between 0.3% and 2%. This low variation indicates that the mixture of the inocula for each batch is homogenous and stable.

The richness measured at the species or genus level is markedly greater in the pooled inocula, in comparison with the individual inocula. On average, the richness increases from 64% in batch No. 4 and by 147% in batches Nos. 1 and 3 in comparison with the individual inocula.

On average, the richness measured at the genus level of the pooled inoculum is increased by 25% for batch No. 4 and by 61% for batches Nos. 1 and 3 in comparison with the individual inocula. The richness of batches 1 to 4 is surprising, and cannot be deduced from the individual richness of the individual inocula; that is to say, this richness of the mixtures of inocula (the pooled inocula) is not the average, whether direct, or weighted by weight of the individual inocula or by fraction of the measured individual richness. This result is unexpected.

The percentage of Proteobacteria present in the four pooled inocula was measured (see Table 5). The values are 5.5%, 3.7%, 3.1% and 3.4% for batches Nos. 1, 2, 3 and 4 respectively.

In conclusion, pooling of the inocula results in an unexpected increase in the richness of the microbiota. Thus, the mixture of inocula is a sample of fecal microbiota having its own characteristics.

Figure 4B:
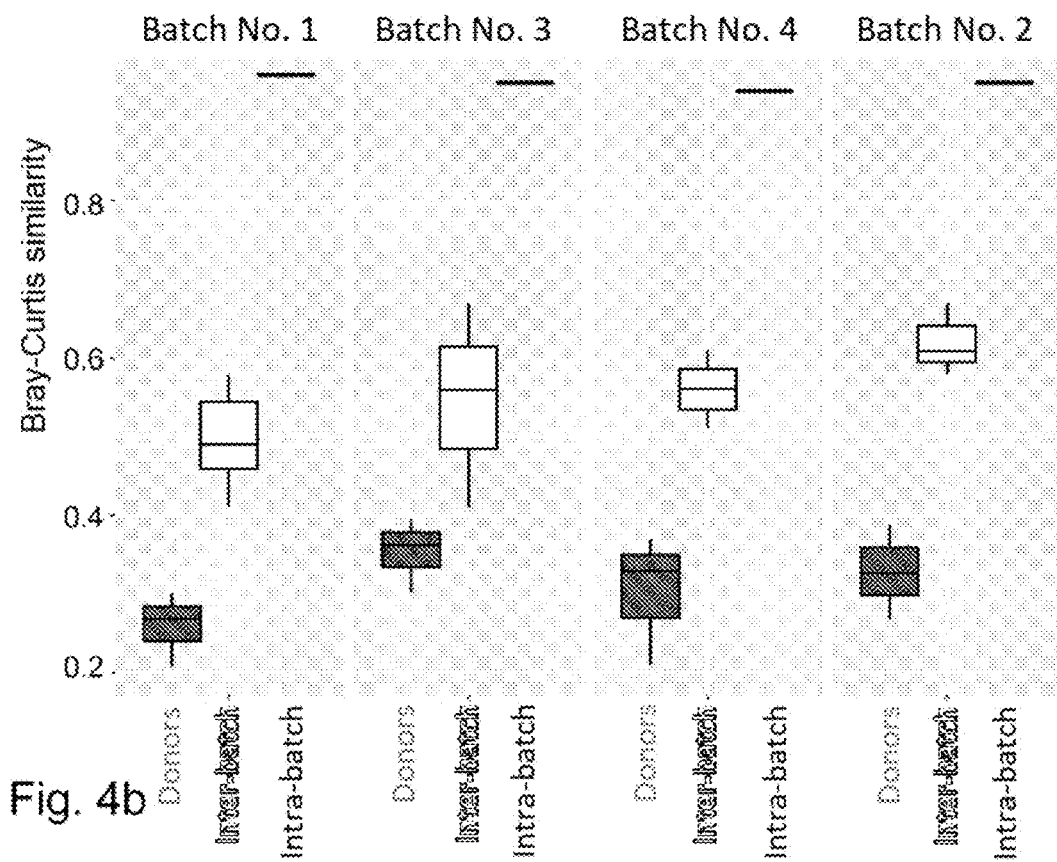

FIG. 4b shows that the method involves standardization of the products (homogenous mixture) obtained for a batch and intended for clinical use. The figure shows that the Bray-Curtis similarity between the pouches (containing the pooled inoculum) for each batch is greater than 96%. This result shows that in terms of taxonomic profile, the pouches of inoculum (the homogenous mixture) are homogenous.

The bacterial diversity was measured by using the Inverse Simpson index and the Shannon index (Table 5).

The results indicate that the Inverse Simpson index for the donors varies between 5 and 30. This difference is normal as each microbiota is different. According to the data presented in Table 5, it may be noted that the Inverse Simpson index for the pooled inoculum is situated between 20.2 and 27.2. The bacterial diversity of the pooled inoculum (after step g)) is higher than that of the individual donors (with the exception of batch No. 3 where the diversity of a donor is greater than that for the pooled inoculum).

The Shannon index is between 2.4 and 4.2 for the donors. This difference is normal as each microbiota is different. The Shannon index for the pooled inoculum is comprised between 4 and 4.50 (see Table 5).

It can also be seen that for each batch the diversity of the pooled inoculum is higher than that of the individual donors. The values obtained, as for the richness, cannot be predicted and constitute for each one a characteristic specific to the homogenous mixture.

The inventors carried out comparative tests to show that in general, the mixture of inocula capable of being obtained according to the method of the invention has advantageous characteristics with respect to the samples of fecal microbiota obtained according to known methods, and in particular, the multi-donor methods. Thus it is described in Example 3 how the inventors characterized samples produced according to the method described in the prior art [Paramsothy S., et al. (2017), Multidonor intensive faecal microbiota transplantation for active ulcerative colitis: a randomized placebo-controlled trial, Lancet, March 25; 389 (10075): 1218-1228] and how they compared them with those produced according to an embodiment of the invention. The two production methods are described in FIG. 5. The samples produced according to an embodiment of the invention showed improved viability and improved diversity with respect to those produced according to the method of the prior art.

The viability of the products was measured. The viability of the pooled inoculum according to an embodiment of the invention changes from 41.8% on average over 5 samples to 41.4% after one month of storage at $-80°$ C.$+/-10°$ C. The samples obtained according to the method of Paramsothy et al. change from 38.5% on average to 37.5%. This change in viability is insignificant according to the Wilcoxon test with p values of 0.462 for the samples according to the invention and a p value of 0.1732 for the reference samples (according to Paramsothy et al.).

However, the Wilcoxon test shows a significant difference in viability between the two groups of samples at T0 (day 0) with a p value equal to 0.01193, as well as at 1 month (p=0.007937).

In addition, the coefficient of variation (CV) for the samples prepared according to the method of the invention at 0 days is 0.010 compared with 0.034 for the reference samples according to the prior art (Paramsothy et al.). At one month, the CV of the samples prepared according to the method of the invention is 0.018 compared with 0.028 for the reference samples. As for Example 1, the inventors have shown that the samples produced for Example 2 have very low variation, which indicates that the mixture of the inocula for each batch is homogenous and stable. By comparison, the reference samples show a higher CV.

The inventors analyzed the microbial diversity of the samples of Example 3 by analyzing the 16S rDNA of the samples. The diversity is expressed with the Inverse Simpson index which takes account of both the richness (the number of OTU/species identified) and the respective relative abundance thereof.

Figure 6B:
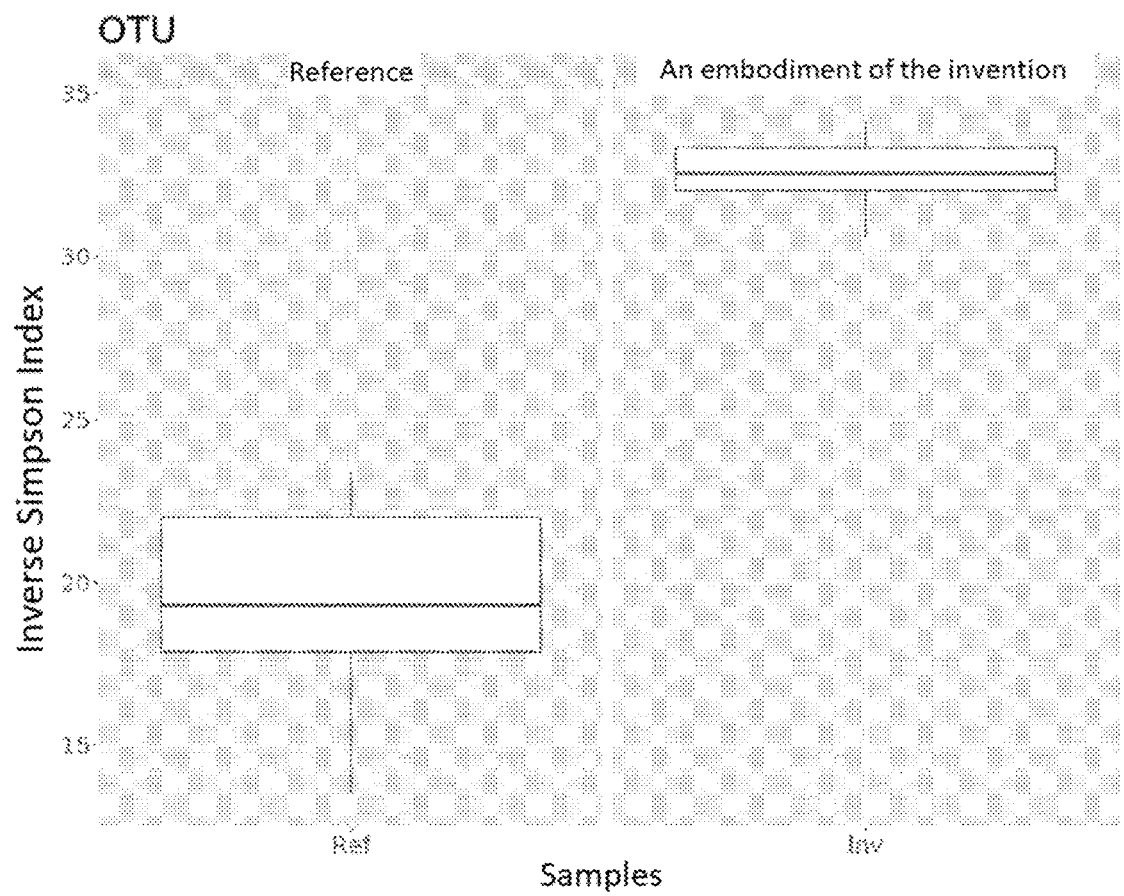

FIG. 6 shows the Inverse Simpson index values comprised between 30.96 and 33.69 (median=32.56) for the samples prepared according to an embodiment of the invention and between 13.70 and 23.18 (median=19.31) for the "Reference" samples prepared according to Paramsothy et al. The diversity observed is thus greater in the samples prepared according to an embodiment of the invention. The samples prepared according to an embodiment of the invention furthermore have improved homogeneity with respect to the "Reference" samples, which is evidenced by the coefficient of variation, 2.7% for the former against 16.1% for the latter. The rank test evaluates a "very highly significant" difference between the two methods (p<2.2e-16).

Figure 7:
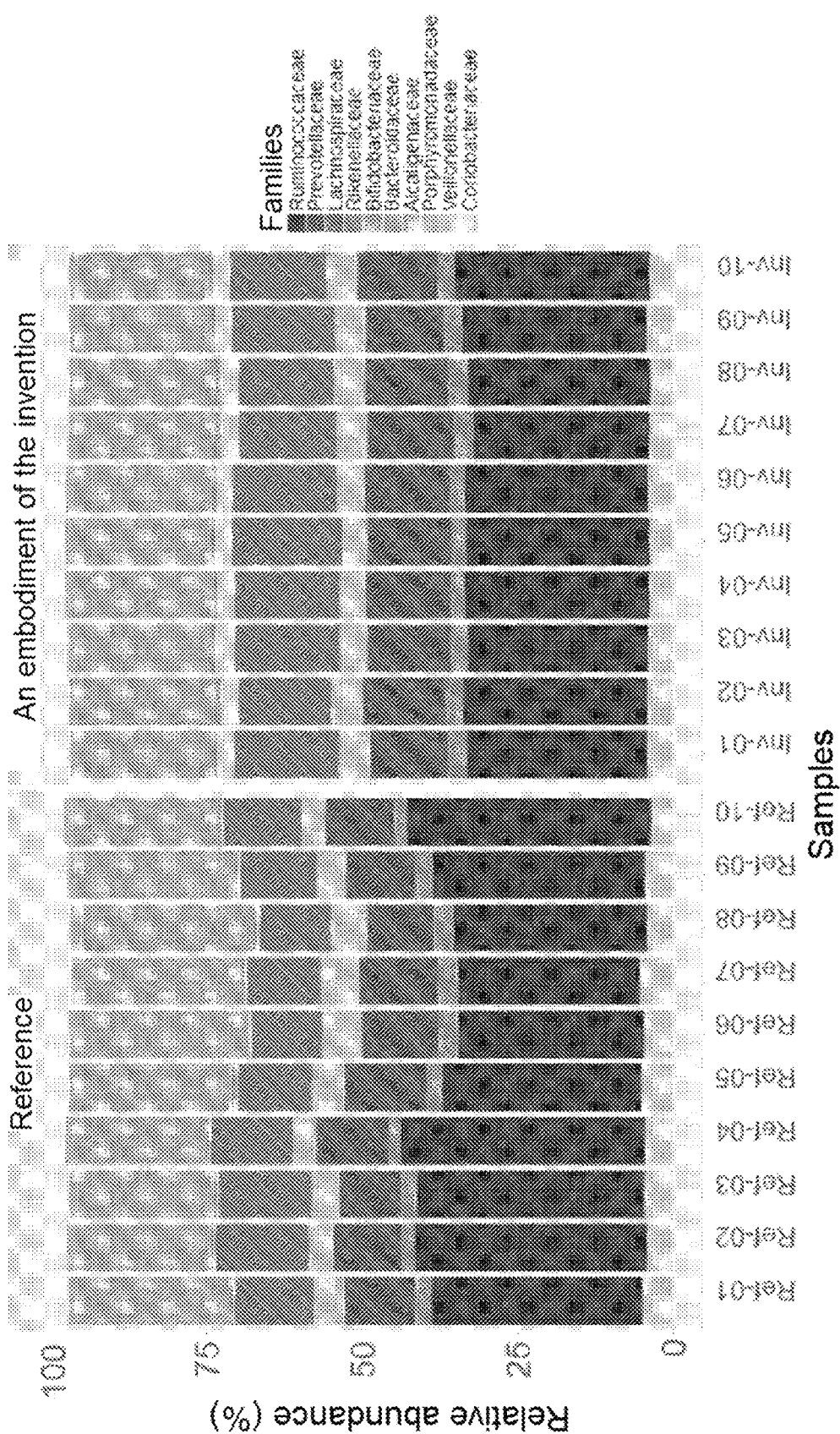
FIG. 7 is a stacked histogram representing the relative abundance of the 10 bacterial families most present in two groups of samples in Example 3. The group on the right (samples Inv-01 to Inv-10) is produced according to an embodiment of the invention. The "Reference" group on the left (samples Ref-01-Ref-10) is produced according to a method of the prior art, Paramsothy et al.

FIG. 7 shows the relative abundance of the 10 bacterial families most present in two groups of samples in Example 3. Samples Inv-01 to Inv-10 have markedly improved homogeneity with respect to samples Ref-01-Ref-10 produced according to a method of the prior art, Paramsothy et al. Although visual, this representation makes it possible to observe the level of heterogeneity generated by the Paramsothy et al. method, as well as the deviation in abundance between the two methods for certain families.

The deviation in homogeneity, diversity and abundance are clearly shown at the different taxonomic levels. Furthermore, as shown in Table 6 of Example 3, the inventors noted that certain bacterial species recognized as favorable for health have improved preservation in samples Inv-01 to Inv-10 in comparison with samples Ref-01-Ref-10. For example, for the Actinobacteria phylum, the relative abundance drops very significantly when using the method according to Paramsothy et al., since this median abundance is 3.6% for samples Inv-01-Inv-10 against 0.9% for samples Ref-01 to Ref-10. In terms of homogeneity, the inventors observed respective coefficients of variation of 7.8% and 14.5%. Furthermore, in FIG. 7, a significant reduction is observed in the relative abundance of the Coriobacteriaceae, a family of the Actinobacteria phylum, between the samples of the invention and the reference samples.

Similar results are observed with the genus *Prevotella* (genus linked to the phylum of the Bacteroidetes) and confirm the differences between the two methods, both with respect to maintenance of certain taxa and as regards homogeneity. The relative abundance of *Prevotella* is higher in Inv-01-Inv-10 samples (median at 13%) with respect to the Ref-01 to Ref-10 samples (median at 11%). In terms of homogeneity, the inventors observed respective coefficients of variation of 3.3% and 8.5%.

Finally, the genus *Bifidobacterium* (belonging to the Actinobacteria) also confirms the results already observed at the other taxonomic levels. The relative abundance of *Bifidobacterium* is found to reduce significantly (0.9% vs 0.6%) and the homogeneity between the samples generated by the Paramsothy et al. method is lower than for those generated by the method according to an embodiment of the invention (see Table 6 of Example 3).

These items thus show that in general, the claimed method allows improved preservation of this phylum, associated with much improved homogeneity at the level of the samples manufactured for each batch; especially the samples manufactured according to an embodiment of the invention compared to those manufactured according to the method of the prior art. This improved homogeneity is of fundamental importance for the characterization of the final product as a pharmaceutical product. Thus, a patient who receives several samples of fecal microbiota from the same batch receives a homogenous product each time having the same diversity and the same microbial viability. This reproducibility is ensured by means of the method used to produce the samples.

In conclusion, the metagenomic analysis (16S rDNA sequencing) of Example 3 made it possible to demonstrate that the samples obtained according to an embodiment of the invention had:
improved preservation of diversity, shown by the very much higher Inverse Simpson index,
significantly greater preservation of certain taxa of interest such as Actinobacteria, which include the well-known genus *Bifidobacterium*,
a greater level of homogeneity between the samples with respect to that obtained for the set of samples produced with the method according to Paramsothy et al.

Figure 9:
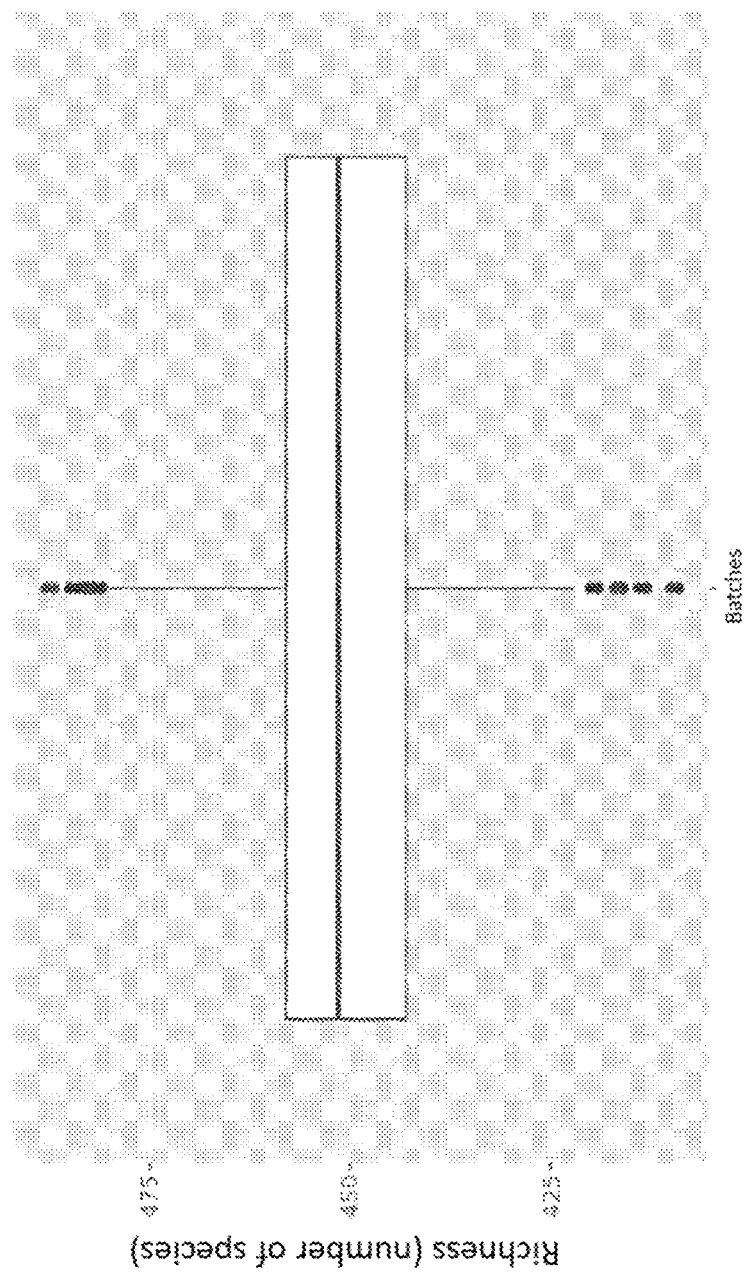
FIG. 9 shows the richness in species in the different batches of homogenous mixture obtained from the stools of 4, 5 and 6 donors.

In general, the method according to the invention has improved reproducibility with respect to that of the prior art, which is very important for a method intended for the manufacture of medicaments, for which the concept of a homogenous and reproducible batch is fundamental to the regulations. The richness values measured for the different batches (see FIG. 9) do in fact show large reproducibility between the batches, with a coefficient of variation of 3.5%. Thus, these results show that there is inter-batch, as well as intra-batch, homogeneity of fecal microbiota. The inventors observed that the mixture of inocula thus obtained has a taxonomic profile and bacterial viability greater than those of certain individual inocula, which means that it is perfectly suitable for use in allogenic FMT (fecal microbiota transfer). The mixture of inocula obtained according to the method of the invention is superior in terms of quality for use in FMT, as it is characterized by a high, stable viability, as well as very high diversity. These characteristics allow a higher potential for recolonization of suitable microbiota with respect to that which would be obtained by using an individual inoculum.

According to a preferred embodiment of the invention, the method for the preparation of the samples of microbiota makes it possible to obtain a homogenous mixture of microbiota comprising 15 butyrate-producing bacterial genera, namely *Blautia, Faecalibacterium, Alistipes, Eubacterium, Bifidobacterium, Ruminococcus, Clostridium, Coprococcus, Odoribacter, Roseburia, Holdemanella, Anaerostipes, Oscillibacter, Subdoligranulum* and *Butyrivibrio*. This embodiment is illustrated in Example 4.

Example 4 describes the experiments intended to obtain homogenous mixtures of stools from eight donors meeting the selection criteria (step c)). Each stool having passed the quality control was then treated separately by addition of cryoprotective diluent, then filtration. The individual inocula obtained on the same day were then mixed so as to obtain homogenous batches of products.

Figure 8:
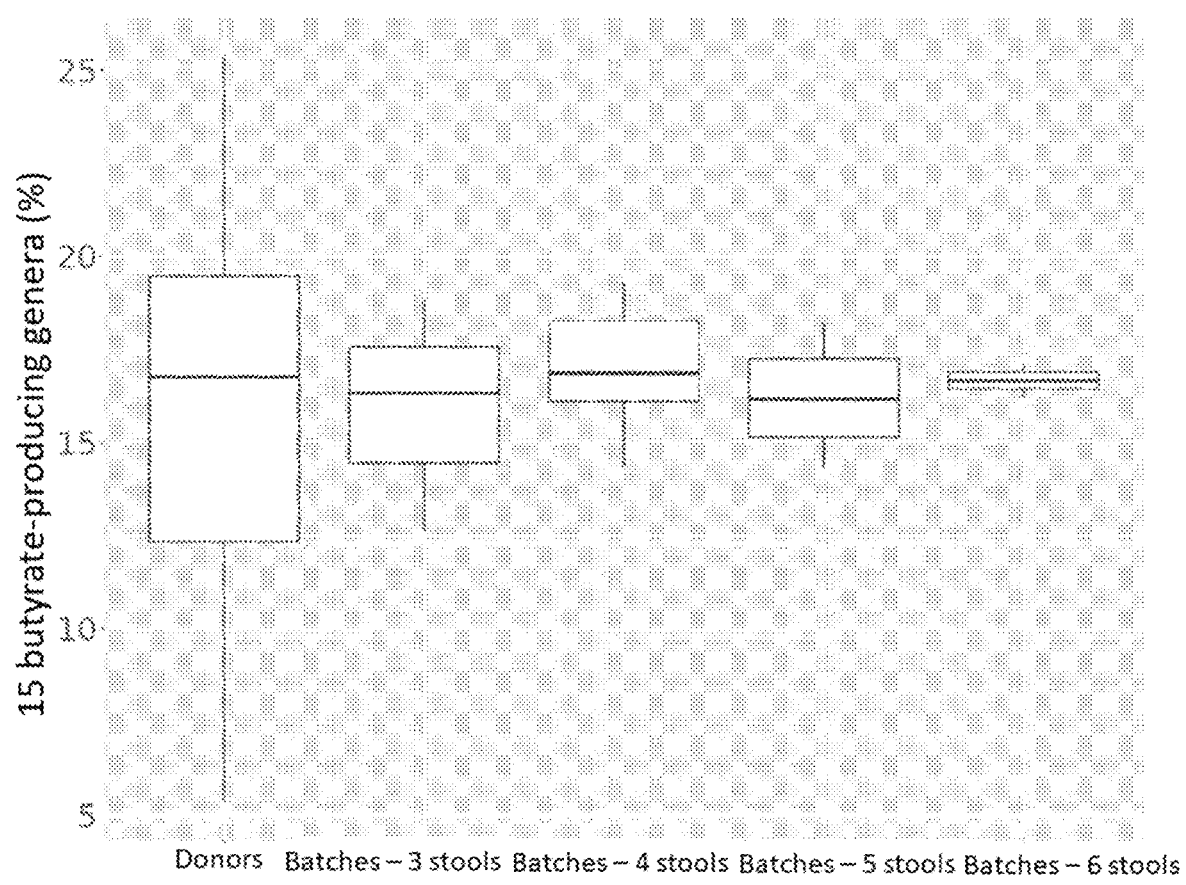
FIG. 8 shows the relative abundance of the 15 butyrate-producing bacterial genera, namely *Blautia, Faecalibacterium, Alistipes, Eubacterium, Bifidobacterium, Ruminococcus, Clostridium, Coprococcus, Odoribacter, Roseburia, Holdemanella, Anaerostipes, Oscillibacter, Subdoligranulum* and *Butyrivibrio*, in the donor stools (first box on the left), then in the batches of the homogenous mixtures obtained from the stools of 3, 4, 5 and 6 donors respectively.

Analysis of the stools of the donors and of the batches of mixtures produced shows that the concentration of the aforementioned 15 butyrate-producing bacterial genera is stable in the mixtures, regardless of the number of stools used for production thereof. The analysis also shows that the abundance of these 15 butyrate-producing bacterial genera standardizes when the number of stools used increases (FIG. 8 and Table 7). In addition, the 15 butyrate-producing bacterial genera are not all found in the individual stools of the donors, while all the batches manufactured with a mixture of at least four stools contain them all.

According to a preferred embodiment of the invention, the method for the preparation of a homogenous mixture of fecal microbiota originates from at least four donors. According to a preferred embodiment of the invention, the homogenous mixture of microbiota comprises the following 15 butyrate-producing bacterial genera, namely *Blautia, Faecalibacterium, Alistipes, Eubacterium, Bifidobacterium, Ruminococcus, Clostridium, Coprococcus, Odoribacter, Roseburia, Holdemanella, Anaerostipes, Oscillibacter, Subdoligranulum* and *Butyrivibrio*.

The presence of the aforementioned 15 butyrate-producing bacterial genera in the product intended to be administered to the patient is important, as these bacterial genera are associated with anti-inflammatory properties. Thus, from a therapeutic point of view, the presence thereof in the homogenous mixtures is advantageous for use of these homogenous mixtures in the treatment of intestinal inflammation, in particular, that associated with intestinal dysbiosis.

The homogenous mixture can be easily produced reliably and reproducibly. The results of Example 1 show homogeneity of viability and taxonomic profile between all the pouches of mixture produced. The quality of the sample of microbiota (the homogenous mixture) administered is reproducible and is identical between pouches originating from a group of donors. An almost identical product can be administered with each pouch. The patient can thus receive the same product at several treatments, if more than one treatment is necessary.

In general, n donors can give sufficient homogenous mixture to fill approximately 3n, preferably 3.2n pouches, each pouch being sufficient for one TMF treatment.

The homogenous mixture of microbiota (or pooled inoculum) can be used in the treatment of intestinal dysbioses and the associated pathologies. In fact, it represents the active ingredient thereof. The bacterial diversity of the pooled inoculum, produced with the method of the invention, is high, being capable of having a Shannon index between 4 and 4.50, and an Inverse Simpson index situated between 20.2 and 27.2. The applicants also showed that the individual inocula have very varied viabilities, but that the inoculum mixture (pooled inoculum) has an excellent viability (from approximately 41% to 60%). According to an embodiment of the invention, the homogenous mixture of inoculum has a viability greater than 40%, preferably greater than 45% and more preferentially greater than 50%, even more preferentially, greater than 55%. The criteria for bacterial diversity and viability are very important in the evaluation of the quality of a product for FMT.

It is also important for the products to be homogenous, according to regulatory criteria for pharmaceutical products. The data in the examples below show that the products according to the invention are homogenous.

According to an embodiment of the invention, the homogenous mixture of microbiota (or pooled inocula) can be administered via the rectal route. According to an embodiment of the invention, the homogenous mixture of microbiota (or pooled inocula) can be formulated for administration via the oral route. There may be mentioned as oral formulation, the formulations mentioned in patent application EP 17306602.8.

As mentioned above, studies show that FMT can be efficacious in the treatment of graft-versus-host disease (GvHD). Thus, the homogenous mixture of microbiota of the invention can be used in the treatment of GvHD. Furthermore, the presence of the 15 aforementioned butyrate-producing bacterial genera can contribute to the efficacy of the treatment of graft-versus-host disease (GvHD). Thus, according to an embodiment of the invention, a patient suffering from GvHD may receive allogenic FMT comprising the homogenous mixture of the invention. For example, the patient may receive allogenic FMT via the rectal route. Also, the patient may receive it via the oral route.

The homogenous mixture of microbiota can be used in the treatment of iatrogenic intestinal dysbiosis and/or associated pathologies and complications comprising septicemia, septic shock and gastrointestinal disorders, including diarrhea, mucitis, abdominal pain and gastrointestinal bleeding. Furthermore, the presence of the 15 aforementioned butyrate-producing bacterial genera having an anti-inflammatory effect can contribute to the efficacy of the treatment.

The homogenous mixture of microbiota can be used in the treatment of *Clostridium difficile* infection and associated diarrhea (CDI), inflammatory bowel disease (IBD), irritable bowel syndrome (IBS), idiopathic constipation, coeliac disease, Crohn's disease, obesity and morbid obesity, autism, multiple sclerosis, traveler's diarrhea, chronic vaginal infection (including cystitis and mycosis), bone and joint infections, Parkinson's disease, type II diabetes, food allergies, cancer, resistant leukemia, Alzheimer's disease, schizophrenia and bipolar disorders, intestinal dysbiosis associated with antineoplastic chemotherapy or immunotherapy and alcohol- or non-alcohol-related liver disease.

The homogenous mixture of microbiota can be used in treatment of complications due to hospitalization in intensive care.

The invention is moreover described with reference to the following examples. It will be understood that the invention as claimed is not intended to be limited in any way whatever by these examples.

EXAMPLES

Example 1

Steps a) and b): Eight fresh stools from six healthy donors were collected in the medical device described in WO2016/170290, then stored at +2° C./+8° C. for a period of 72 hours, during which time quality controls (step c)) were carried out. On the basis of the results of these controls, the stools from donors 3 and 7 were rejected.

Stools 1, 4, 5, 6 and 2+8 were separately transformed into a liquid inoculum by adding cryoprotective diluent (aqueous saline solution containing a mixture of maltodextrin and trehalose at 20%) and clarified through a filter (265 μm). Stools 2 and 8 were combined to form an inoculum, given the small quantities of stools taken.

The viability of inocula 1, 4, 5, 6 and 2+8 (five inocula) was tested. The individual inocula were then transferred to a 5 L flexible pouch by using a peristaltic pump. The pouch was then placed on a stirring plate in a refrigerated incubator set to 4° C. and mixing of the inoculum was carried out at 125 rpm+/−5% for 30 minutes.

After the homogenization was finished, the mixture of inoculum was transferred to a series of 15 pouches suitable for lyophilization and stored at −80° C. The viability and the impact of storage of the homogenous mixture under different conditions were tested for each of the 15 pouches before storage.

Analysis of Viability:

Viability tests were carried out by using flow cytometry technology using an Accuri 6 cytometer (BD Science). The samples were diluted in an aqueous saline solution at 0.9%, with serial dilution 1:10, up to $1:10^{-3}$. The samples were stained with propidium iodide fluorophores (PI) (104/mL) and SYTO9® 9 (34/mL). The PI also targets DNA, but only penetrates into the cells the membranes of which are damaged; it emits at 635 nm (red) after excitation at 470 nm. SYTO9® enters all the cells, whether undamaged or not, binds to the DNA and emits at 540 nm (green) after excitation at 470 nm (blue laser). The samples of stools, inoculum or homogenous mixture are labeled with the mixture of the two fluorophores before being analyzed by flow cytometry. The percentage of live bacteria with respect to the total number of bacteria (live and dead) makes it possible to obtain the bacterial viability of the sample. Each batch of the analysis was validated with a positive control (reference sample of inoculum stored at −80° C.) and a negative control (reference sample stored at −80° C. and treated by incubation of 10 minutes in 70% isopropanol (ratio 1/9), centrifuged, placed in suspension in 0.9% NaCl and diluted in serial dilution 10 times up to $10^{-3}$).

Results:

Evaluation of the viability of the individual inocula varies from 30.5% to 67.6%. The 15 pouches prepared with the same mixtures of inocula show an average viability of 47.1% with a standard deviation of 1.98. The percentages of viability of the microbiota of the individual inocula (inoculum 1, 4, 5, 6 and 2+8, colored light gray) and of the mixture of inoculum in storage pouch 1 to 15 (colored black) are presented in FIG. 2.

The summary results are presented in Table 1.

TABLE 1

Summary of the viability of the microbiota of the allogenic inoculum analyzed

| Analyses | Viability (%) |
|---|---|
| Average | 47.1 |
| Standard deviation | 1.98 |
| Min | 44.3 |
| Max | 51.4 |

Statistical Analysis:

The viability and number of events were measured on the 15 pouches of homogenous mixture. In order to evaluate if these two measurements were homogenous between the pouches, a random allocation of measurements to Group A for 7 pouches and to Group B for the remaining pouches was carried out 500 times.

For each iteration, a t-test and a rank test were used to compare Group A to Group B. The final results presented below correspond to the proportion of iterations where the statistical test in question was insignificant (>0.1).

The conclusion is that the pouches are homogenous in terms of viability and in terms of the number of events/µL.

TABLE 2

Statistical results

| Test | Viability | Number of events/µL |
|---|---|---|
| Proportion of iterations where the t-test is insignificant | 93.4% | 95.4% |
| Proportion of iterations where the rank test is insignificant | 95.4% | 96.8% |

The results show that there is no significant difference for the t-test and the rank test, whether for the viability of the microbiota or for the number of events/A.

It can be concluded that the 15 prepared pouches of mixture are mutually homogenous.

Preservation:

During the method for preparation of the mixture, intermediate storage must be carried out while the quality controls are performed. In order to determine the impact of this intermediate storage on the viability of the microbiota, an evaluation was carried out:

control condition: after preparation, the inoculum is immediately stored at −80° C.

condition of preservation at ambient temperature: after preparation, the inoculum is kept at ambient temperature for 16 hours, sampling is carried out in order to determine the viability of the microbiota, the microbiota events/µL and the measurement of the pH and of the $PO_2$, then the inoculum is stored at −80° C.

condition of preservation at 4° C.: after preparation, the inoculum is stored at 4° C. for 16 hours, sampling is carried out in order to determine the viability of the microbiota, the microbiota events/µL and the measurement of the pH and of the $PO_2$, then the inoculum is stored at −80° C.

Then, the three inocula are defrosted and the viability of the microbiota is measured.

The data show that the median viability of the microbiota is the same whether the inoculum is stored for 16 hours at ambient temperature or at 4° C. After defrosting, the median viability of the microbiota is reduced for the inoculum, whether stored at 4° C. or at ambient temperature. It is expected for the viability to drop after freezing. It is noted here that in both cases (4° C. and ambient temperature) the same phenomenon is observed.

It can be observed that the number of events/4 is the same for the inoculum and for the inoculum stored at 4° C., but as would be expected, it increases for the inoculum stored at ambient temperature. The same observation is made after defrosting of the inoculum.

All these results show that storage for 16 hours has no impact on the viability of the microbiota whether stored at 4° C. or at ambient temperature; the number of events/µL increases at ambient temperature, indicating that the microbiota is developing, while at 4° C. the microbiota is in the latent state. The results of measurement of the pH and of the $PO_2$ are shown in Table 3.

TABLE 3

Results of measurement of the pH and of the $PO_2$

| Sample | PH | $PO_2$ (%) |
|---|---|---|
| Inoculum | 6.33 | 1.4 |
| Storage for 16 h at ambient temperature | 5.34 | 4.3 |
| Storage for 16 h at 4° C. | 6.28 | 1.6 |
| Defrosting control | 6.55 | 1.5 |
| Defrosting the inoculum stored for 16 h at ambient temperature | 5.29 | 3.7 |
| Defrosting the inoculum stored for 16 h at 4° C. | 6.23 | 1.3 |

These results show that storage for 16 hours has no impact on the pH or the $PO_2$ of the inoculum stored at 4° C.

Example 2

By using almost the same conditions as for Example 1, the method was carried out on four batches of fecal microbiota samples (batch No. 1 to batch No. 4) with 2, 8, 4 and 6 donors for batch No. 1, batch No. 2, batch No. 3 and batch No. 4, respectively. Batch No. 4 corresponds to the batch in Example 1. Thus, for batch No. 4, two of the six stools were combined to form an inoculum, given the small quantities of stools taken.

The stools were separately transformed into a liquid inoculum by adding cryoprotective diluent (aqueous saline solution containing a mixture of maltodextrin and trehalose at 20%) and clarified through a filter (265 µm).

The viability and the taxonomic profile of the inocula were tested. The individual inocula were then transferred to a 3 L or 5 L flexible pouch by using a peristaltic pump. The pouch was then placed on a stirring plate in a refrigerated incubator set to 4° C. and mixing the inoculum was carried out at 130 rpm+/−5% for 30 minutes in an incubator set to 4° C.

After the homogenization was finished, for each batch, the mixture of inoculum was transferred to a series of pouches suitable for freezing and stored at −80° C. The viability and the taxonomic profile of the homogenous mixtures were tested before storage. For batch No. 1, 2 stools were collected and 5 pouches were filled. For batch No. 2, 8 stools were collected and 29 pouches were filled. For batch No. 3, 5 stools were collected and 21 pouches were filled. For batch No. 4, 6 stools were collected, 2 stools were combined in order to have enough material to form an inoculum and 15 pouches were filled.

Analysis of Viability:

The viability tests were carried out as for Example 1.

Metagenomic Analysis:

The genomic DNA was extracted from the samples with the NucleoSpin Soil kit (Machery Nagel). A sequencing library was compiled for each sample with the MyTaq HS-Mix kit (Bioline). The libraries were then sequenced on a MiSeq V3 2×300 pb run.

After quality control of the demultiplexed sequences with Trimmomatic [Bolger et al., (2014) 'Trimmomatic: A flexible trimmer for Illumina sequence data', Bioinformatics, 30(15), pp. 2114-2120. doi: 10.1093/bioinformatics/btu170], the human sequences were eliminated using the Bowtie2 software (Langmead, Ben and Salzberg, (2013) 'Fast gapped-read alignment with Bowtie2', Nature methods, 9(4), pp. 357-359. doi: 10.1038/nmeth.1923.Fast). In order to allow comparison of the data, the number of sequences was normalized to 60,000 sequences per sample. Clustering of the sequences was carried out with VSEARCH and the taxonomic allocation was then performed using the Silva 128 database. The taxonomic analyses and the measurements of diversity were carried out with R software (R Core Team 2015, version 3.4.4, http://www.R-project.org). For the measurements of diversity, 20 sub-samplings of 60,000 sequences were carried out for each sample and the median was measured.

Results:

Viability:

Table 4 below shows the viability of the batches. Evaluation of the viability of the individual inocula varies from 16.8% to 67.6%. Viability of the pooled batches of inocula is given in the Table below and is situated between 46.1 and 60.2%.

TABLE 4

| Analyses | Batch No. 1 | Batch No. 2 | Batch No. 3 | Batch No. 4 |
|---|---|---|---|---|
| Number of donors | 2 | 7 | 4 | 6 |
| Average (%) | 60.2 | 46.1 | 53.2 | 47.1 |
| Standard deviation | 1.2 | 1.1 | 2.1 | 2.0 |
| Min | 59.4 | 45.0 | 50.6 | 44.3 |
| Max | 61.6 | 48.3 | 58.2 | 51.4 |

Table 5 below shows the results.

TABLE 5

| | Analyses | Inverse Simpson index | Shannon | Proteobacteria |
|---|---|---|---|---|
| Batch No. 1 | Donor 1 | 17.68 | 3.8 | |
| | Donor 2 | 8.23 | 2.6 | |
| | Mixture of inocula | 20.2 | 4 | 5.6 |
| Batch No. 2 | Donor 1 | 17.4 | 3.9 | |
| | Donor 2 | 7.5 | 3 | |
| | Donor 3 | 16.4 | 3.5 | |
| | Donor 4 | 16.3 | 3.48 | |
| | Donor 5 | 26 | 3.8 | |
| | Donor 6 | 12.4 | 3.4 | |
| | Donor 7 | 22.07 | 4 | |
| | Mixture of inocula | 26.2 | 4.3 | 3.5 |

TABLE 5-continued

| | Analyses | Inverse Simpson index | Shannon | Proteobacteria |
|---|---|---|---|---|
| Batch No. 3 | Donor 1 | 21.06 | 3.98 | |
| | Donor 2 | 29.15 | 4.1 | |
| | Donor 3 | 20.28 | 3.7 | |
| | Donor 4 | 6.5 | 2.5 | |
| | Mixture of inocula | 27.2 | 4.3 | 3.7 |
| Batch No. 4 | Donor 1 | 12.3 | 3.59 | |
| | Donor 4 | 16.37 | 4.1 | |
| | Donor 5 | 21.37 | 3.48 | |
| | Donor 6 | 16.71 | 4 | |
| | Donor 2 + Donor 8 | 25.12 | 3.52 | |
| | Mixture of inocula | 26.4 | 3.27 | 3.1 |

Example 3

Figure 5:
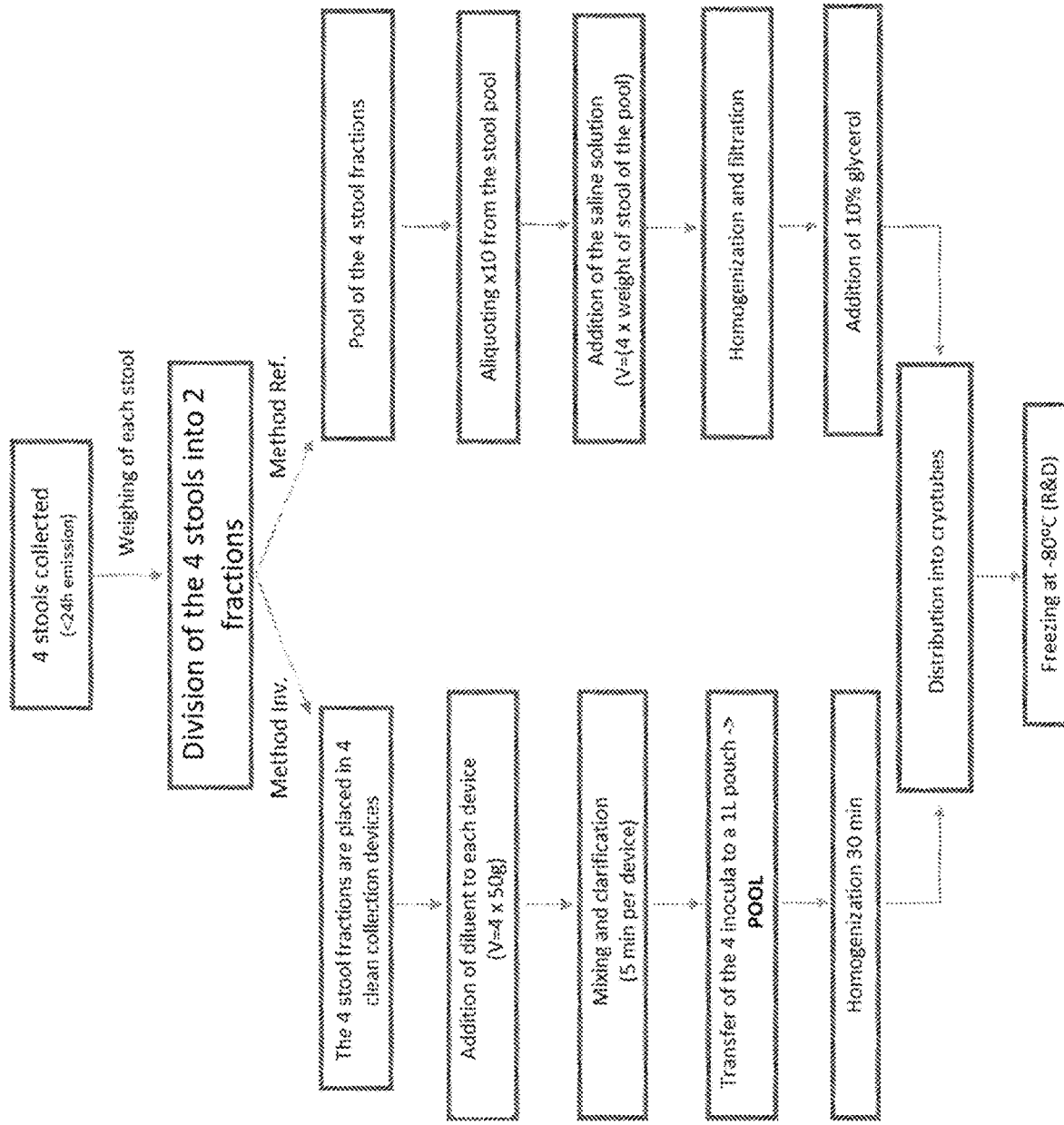
FIG. 5 is a diagrammatic representation of the comparative experiments in Example 3, in which the same stools were used in order to carry out the two manufactures of batches of samples, one manufacture according to an embodiment of the invention ("Method Inv"), identical to the method described for Example 3, and one manufacture according to the method described in Paramsothy et al. [Paramsothy S., et al. (2017), Multidonor intensive fecal microbiota transplantation for active ulcerative colitis: a randomised placebo-controlled trial, Lancet, March 25; 389 (10075): 1218-1228], or "Ref Method".

The purpose of this study is to compare two methods for the preparation of samples of fecal microbiota from multiple donors:

the method described in Example 2 and the method of the prior art by Paramsothy et al. [Paramsothy S., et al. (2017), Multidonor intensive faecal microbiota transplantation for active ulcerative colitis: a randomised placebo-controlled trial, Lancet, March 25; 389(10075): 1218-1228]. FIG. 5 shows the two methods used.

Viability analyses and metagenomic analyses were carried out in order to compare the viability of the final products obtained, as well as the taxonomic homogeneity thereof.

Four fresh stools from four healthy donors were each collected in the medical device described in WO2016/170290, then stored at +2° C./+8° C. for a period of 72 hours, during which quality controls (step c)) were carried out.

The four stools were divided into two fractions, one intended for treatment according to an embodiment of the invention ("Inv") and the other according to the method of the prior art by Paramsothy et al. ("Ref").

The stools ("Inv") were separately transformed into a liquid inoculum by adding cryoprotective diluent (aqueous saline solution containing a mixture of maltodextrin and trehalose at 20%) and clarified through a filter (265 µm).

The individual inocula were then transferred to a 1 L flexible pouch by using a peristaltic pump. The pouch was then placed on a stirring plate in a refrigerated incubator set to 4° C. and mixing the inoculum was carried out at 125 rpm+/−5% for 30 minutes.

After the homogenization was finished, the mixture of inoculum was transferred to a series of 10 cryotubes and stored at −80° C.

The "Ref" stools were mixed so as to obtain a visually homogenous product, clarified in an isotonic saline solution (0.9% NaCl), then filtered. 10% glycerol was then added to the preparation for storage. Then, the sample thus produced was transferred to a series of 10 cryotubes and stored at −80° C.

The viability and 16S metagenomic analysis were carried out as described in Example 2. Comments on the results are given in the text below.

Table 6 shows the relative abundance of *Actinobacteria*, *Prevotella* and *Bifidobacteria* in the "Inv" and "Ref" samples.

TABLE 6

|  | Relative abundance | | Coefficient of Variation | | Wilcoxon |
| --- | --- | --- | --- | --- | --- |
|  | Inv | Ref | Inv | Ref | Rank Test |
| *Actinobacteria* | 3.6% | 0.9% | 7.8% | 14.5% | $1.083^e-5$ |
| *Prevotella* | 13% | 11% | 3.3% | 8.5% | $2.057^e-4$ |
| *Bifidobacteria* | 0.9% | 0.6% | 12.4% | 13.9% | $1.083^e-5$ |

Example 4

A production campaign intended to obtain homogenous mixtures of stools was carried out as described in Example 1. The stools from 8 donors meeting the selection criteria of step c) were collected daily over a period of 5 weeks. The stools were separately transformed into a liquid inoculum by adding cryoprotective diluent (aqueous saline solution containing a mixture of maltodextrin and trehalose at 20%) and clarified through a filter (265 µm).

The individual inocula obtained on the same day were then mixed so as to obtain homogenous batches of products.

DNA Extraction, Metagenomic Sequencing and Bioinformatic Analysis

The genomic DNA was extracted from the mixtures of stools with the NucleoSpin Soil kit (Machery Nagel). A sequencing library was compiled for each sample of genomic DNA, using the TruSeq kit (Illumina) according to the supplier's recommendations. The libraries were then sequenced simultaneously as a "paired-end" run on a HiSeq2500 (Illumina).

After quality control of the demultiplexed sequences with Trimmomatic [Bolger et al., (2014) 'Trimmomatic: A flexible trimmer for Illumina sequence data', Bioinformatics, 30(15), pp. 2114-2120. doi: 10.1093/bioinformatics/btu170], the human sequences were eliminated using the Bowtie2 software (Langmead, Ben and Salzberg, (2013) 'Fast gapped-read alignment with Bowtie2', Nature methods, 9(4), pp. 357-359. doi: 10.1038/nmeth.1923.Fast). In order to allow comparison of the data, the number of sequences was normalized to 20,000,000 "paired-end" sequences per sample. Taxonomic allocation was then carried out with Kraken v.0.10.5-beta (Wood and Salzberg, 2014 Kraken: ultrafast metagenomic sequence classification using exact alignments', Genome Biology, 15(3), pp. R46. doi: 10.1186/gb-2014-15-3-r46) using the RefSeq genome database (September 2017, http://www.ncbi.nlm.nih.gov/refseq/).

Results:

FIG. 8 shows the relative abundance of the 15 butyrate-producing bacterial genera, namely *Blautia, Faecalibacterium, Alistipes, Eubacterium, Bifidobacterium, Ruminococcus, Clostridium, Coprococcus, Odoribacter, Roseburia, Holdemanella, Anaerostipes, Oscillibacter, Subdoligranulum* and *Butyrivibrio*, in the donor stools (first bar on the left), then in the batches of the homogenous mixtures obtained from the stools of 3, 4, 5 and 6 donors respectively. The relative abundance of these genera is stable in each batch and standardizes when the number of stools used in order to obtain the homogenous mixture increases (see Table 7 below)

TABLE 7

Coefficients of variation of 15 butyrate-producing bacterial genera in donors and in the different lots

| Donors | Batches of 3 stools | Batches of 4 stools | Batches of 5 stools | Batches of 6 stools |
| --- | --- | --- | --- | --- |
| 0.376 | 0.196 | 0.093 | 0.086 | 0.039 |

Although the 15 butyrate-producing bacterial genera are not all found in all the individual stools, on the other hand, the batches manufactured with a mixture of at least four stools contain them all (data not shown).

The invention claimed is:

1. A method for the preparation of a homogenous mixture of fecal microbiota originating from at least two preselected donors comprising the following steps:
    a) taking at least one sample of fecal microbiota from said at least two preselected donors,
    b) placing the sample obtained in a) in an oxygen-impermeable collection device within a time period of less than 5 minutes after taking the sample,
    c) performing quality control of the samples taken based on quality criteria, and excluding samples that do not meet the quality criteria,
    d) adding an aqueous saline solution comprising at least one cryoprotectant and/or a bulking agent to each of the samples retained after the quality control step c),
    e) filtering the samples obtained at the end of step d) to form a series of inocula,
    f) grouping said inocula to form a mixture of inocula, and
    g) homogenization of said mixture obtained in step f) to obtain a homogenous mixture,
    wherein steps b) and d) to g) are carried out under anaerobic conditions.

2. The method according to claim 1, wherein the homogenous mixture of fecal microbiota originates from at least four donors.

3. The method according to claim 1, wherein the donors are preselected according to the following preselection criteria:
    i) age ranging from 18 to 60 years,
    ii) body mass index (BMI) ranging from 18 to 30,
    iii) absence of personal medical history of infectious diseases, metabolic and neurological disorders, or depression,
    iv) absence of taking medicaments capable of degrading the composition of the intestinal microbiota,
    v) absence of occurrence of symptoms associated with a gastrointestinal disease,
    vi) absence of travel in tropical countries,
    vii) absence of at-risk sexual behavior,
    viii) absence of wound, piercing and/or tattoo,
    ix) absence of chronic fatigue,
    x) absence of allergic reaction, and
    xi) optionally, having a varied diet.

4. The method according to claim 1, wherein the quality criteria of the samples of step c) comprise:
    consistency of the sample ranging from 1 to 6 on the Bristol scale, and
    absence of blood or urine in the sample.

5. The method according to claim 4, wherein the quality criteria of the samples of step c) further comprise:
    absence of the following bacteria: *Campylobacter, Clostridium difficile, Salmonella, Yersinia enterocolitica, Vibrio* sp., Shiga toxin-producing *E. coli* (STEC) stx1/stx2, multi-resistant bacteria, bacteria producing extended-spectrum beta-lactamases (ESBL) glycopeptide/vancomycin resistant Enterococci (GRE/VRE) and *Listeria monocytogenes*, absence of the following parasites: *Cryptosporidium parvum, Cyclospora* sp., *Entamoeba histolytica, Giardia lamblia, Blastocystis hominis*, Helminths, *Strongyloides stercoralis, Isospora* sp., *Microsporidia* and *Dientamoeba fragilis*, absence of the following viruses: adenovirus F40/41, astrovirus, norovirus, rotavirus A, sapovirus and picornavirus, and absence of the following bacteria: enteroaggregative *E. coli* (EAEC), enteropathogenic *E. coli* (EPEC), enterotoxigenic *E. coli* (ETEC) lt/st, *Shigella*/enteroinvasive *E. coli* (EIEC) and *Plesiomonas shigelloides*.

6. The method according to claim 5, wherein picornavirus is aichi virus and/or enterovirus.

7. The method according to claim 4, wherein the quality criteria of the samples of step c) further comprise:

absence of the following bacteria: *Campylobacter, Clostridium difficile, Salmonella, Yersinia enterocolitica, Vibrio* sp., Shiga toxin-producing *E. coli* (STEC) stx1/stx2, multi-resistant bacteria, bacteria producing extended-spectrum beta-lactamases (ESBL) glycopeptide/vancomycin resistant Enterococci (GRE/VRE), *Listeria monocytogenes*, and carbapenem-resistant bacteria, absence of the following parasites: *Cryptosporidium parvum, Cyclospora* sp., *Entamoeba histolytica, Giardia lamblia, Blastocystis hominis*, Helminths, *Strongyloides stercoralis, Isospora* sp., *Microsporidia* and *Dientamoeba fragilis*, absence of the following viruses: adenovirus F40/41, astrovirus, norovirus, rotavirus A, sapovirus and picornavirus, and absence of the following bacteria: enteroaggregative *E. coli* (EAEC), enteropathogenic *E. coli* (EPEC), enterotoxigenic *E. coli* (ETEC) lt/st, *Shigella*/enteroinvasive *E. coli* (EIEC) and *Plesiomonas shigelloides*.

8. The method according to claim 7, wherein picornavirus is aichi virus and/or enterovirus.

9. The method according to claim 1, wherein the at least one cryoprotectant and/or bulking agent is a polyol, a di-, tri- or polysaccharide or mixture thereof and a bulking agent.

10. The method according to claim 1, wherein the aqueous saline solution comprises maltodextrin and trehalose.

11. The method according to claim 1, wherein the filtration in step e) is carried out with a filter comprising pores of diameter less than or equal to 0.5 mm.

12. The method according to claim 1, wherein the time between the beginning of step a) and the end of step g) is less than 76 hours.

13. The method according to claim 1, wherein step g) of homogenization is carried out at a temperature ranging from 2° C. to 25° C.

14. The method according to claim 1, further comprising
h) transferring the homogenized mixture obtained in step g):
  i) to inoculum pouches for storage at a temperature of approximately −50° C. to −80° C., or for storage at a temperature ranging approximately from 2 to 6° C. for use of the mixture within approximately 16 hours, or for storage at a temperature ranging from 10 to 25° C. for use of the mixture within approximately 4 hours, or
  ii) to a lyophilization device for lyophilization.

15. The method according to claim 1, wherein the homogenous mixture of fecal microbiota comprises the following bacterial genera Blautia, *Faecalibacterium, Alistipes, Eubacterium, Bifidobacterium, Ruminococcus, Clostridium, Coprococcus, Odoribacter, Roseburia*, Holdemanella, Anaerostipes, Oscillibacter, Subdoligranulum and *Butyrivibrio*.

* * * * *